US009397524B2

(12) United States Patent
Kuennen et al.

(10) Patent No.: US 9,397,524 B2
(45) Date of Patent: Jul. 19, 2016

(54) INDUCTIVELY COUPLED BALLAST CIRCUIT

(71) Applicant: Access Business Group International LLC, Ada, MI (US)

(72) Inventors: Roy W. Kuennen, Caledonia, MI (US); David W. Baarman, Fennville, MI (US); Scott A. Mollema, Rockford, MI (US); Ronald C. Markham, Grand Rapids, MI (US); Dennis J. Denen, Westerville, OH (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 15/048,141

(22) Filed: Feb. 19, 2016

(65) Prior Publication Data
US 2016/0172907 A1    Jun. 16, 2016

Related U.S. Application Data

(60) Continuation of application No. 14/089,985, filed on Nov. 26, 2013, now Pat. No. 9,299,493, which is a continuation of application No. 13/233,131, filed on Sep. 15, 2011, now Pat. No. 8,618,749, which is a
(Continued)

(51) Int. Cl.
*H05B 41/36*    (2006.01)
*H05B 37/02*    (2006.01)

(52) U.S. Cl.
CPC ............ *H02J 50/10* (2016.02); *H05B 37/0209* (2013.01)

(58) Field of Classification Search
USPC ............. 315/209 R, 219, 177, 220, 225, 224, 315/291, 307, 308, 248, 276, 283
See application file for complete search history.

(56) References Cited

U.S. PATENT DOCUMENTS 4,076,996 A    2/1978  Maehara et al.
4,469,988 A    9/1984  Cronin
(Continued)

FOREIGN PATENT DOCUMENTS

EP    0 178 852    4/1986
EP    0 267 009    5/1988
(Continued)

OTHER PUBLICATIONS

US 46581874, 04/1987, Grubbs (withdrawn).
(Continued)

*Primary Examiner* — Douglas W Owens
*Assistant Examiner* — Jianzi Chen
(74) *Attorney, Agent, or Firm* — Warner Norcross & Judd LLP

(57) ABSTRACT

A ballast circuit is disclosed for inductively providing power to a load. The ballast circuit includes an oscillator, a driver, a switching circuit, a resonant tank circuit and a current sensing circuit. The current sensing circuit provides a current feedback signal to the oscillator that is representative of the current in the resonant tank circuit. The current feedback signal drives the frequency of the ballast circuit causing the ballast circuit to seek resonance. The ballast circuit preferably includes a current limit circuit that is inductively coupled to the resonant tank circuit. The current limit circuit disables the ballast circuit when the current in the ballast circuit exceeds a predetermined threshold or falls outside a predetermined range.

29 Claims, 15 Drawing Sheets

Related U.S. Application Data continuation of application No. 12/036,348, filed on Feb. 25, 2008, now Pat. No. 8,222,827, which is a continuation of application No. 11/563,882, filed on Nov. 28, 2006, now Pat. No. 7,385,357, which is a division of application No. 10/972,169, filed on Oct. 22, 2004, now Pat. No. 7,180,248, which is a continuation of application No. 10/246,155, filed on Sep. 18, 2002, now Pat. No. 6,825,620, which is a continuation-in-part of application No. 10/175,095, filed on Jun. 18, 2002, now Pat. No. 6,673,250, which is a continuation-in-part of application No. 09/592,194, filed on Jun. 12, 2000, now Pat. No. 6,436,299.

(60) Provisional application No. 60/140,159, filed on Jun. 21, 1999, provisional application No. 60/140,090, filed on Jun. 21, 1999.

(56) References Cited

U.S. PATENT DOCUMENTS

| | | | |
|---|---|---|---|
| 4,914,539 A | 4/1990 | Turner et al. | |
| 5,122,729 A | 6/1992 | Itoga et al. | |
| 5,173,643 A | 12/1992 | Sullivan et al. | |
| 5,191,302 A | 3/1993 | Rossnick | |
| 5,324,423 A | 6/1994 | Markham | |
| 5,325,046 A | 6/1994 | Young et al. | |
| 5,367,242 A | 11/1994 | Hulman | |
| 5,450,305 A | 9/1995 | Boys et al. | |
| 5,455,466 A | 10/1995 | Parks et al. | |
| 5,476,488 A | 12/1995 | Morgan et al. | |
| 5,596,567 A | 1/1997 | deMuro et al. | |
| 5,734,254 A | 3/1998 | Stephens | |
| 5,747,942 A | 5/1998 | Ranganath | |
| 5,777,861 A | 7/1998 | Shimizu et al. | |
| 5,796,334 A | 8/1998 | Chen et al. | |
| 5,853,572 A | 12/1998 | Kuennen et al. | |
| 5,892,458 A | 4/1999 | Anderer et al. | |
| 5,896,278 A | 4/1999 | Tamura et al. | |
| 5,905,372 A | 5/1999 | Kuffner et al. | |
| 5,954,984 A | 9/1999 | Ablah et al. | |
| 5,963,012 A | 10/1999 | Garcia et al. | |
| 6,072,362 A | 6/2000 | Lincoln | |
| 6,118,249 A | 9/2000 | Brockmann et al. | |
| 6,141,227 A | 10/2000 | Sheikh et al. | |
| 6,157,258 A | 12/2000 | Adishian et al. | |
| 6,184,651 B1 | 2/2001 | Fernandez et al. | |
| 6,208,497 B1 | 3/2001 | Seale et al. | |
| 6,232,585 B1 | 5/2001 | Clothier et al. | |
| 6,255,635 B1 | 7/2001 | Thompson et al. | |
| 6,271,508 B1 | 8/2001 | Thompson et al. | |
| 6,274,856 B1 | 8/2001 | Clothier et al. | |
| 6,316,753 B2 | 11/2001 | Clothier et al. | |
| 6,316,756 B1 | 11/2001 | Thompson et al. | |
| 6,320,169 B1 | 11/2001 | Clothier | |
| 6,348,679 B1 | 2/2002 | Ryan et al. | |
| 6,359,267 B1 | 3/2002 | Wilcox et al. | |
| 6,444,961 B2 | 9/2002 | Clothier et al. | |
| 6,504,135 B2 | 1/2003 | Clothier et al. | |
| 6,521,874 B2 | 2/2003 | Thompson et al. | |
| 6,600,142 B2 | 7/2003 | Ryan et al. | |
| 6,617,557 B1 | 9/2003 | Ryan et al. | |
| 6,649,888 B2 | 11/2003 | Ryan et al. | |
| 6,657,170 B2 | 12/2003 | Clothier | |
| 6,664,520 B2 | 12/2003 | Clothier | |
| 6,664,881 B1 | 12/2003 | Thompson et al. | |
| 6,730,894 B2 | 5/2004 | Thompson et al. | |
| 6,774,346 B2 | 8/2004 | Clothier | |
| 6,812,445 B2 | 11/2004 | Gorbold | |
| 6,822,204 B2 | 11/2004 | Clothier | |
| 6,825,620 B2 | 11/2004 | Kuennen et al. | |
| 6,861,629 B2 | 3/2005 | Dahake et al. | |
| 6,934,167 B2 | 8/2005 | Jang et al. | |
| 6,953,919 B2 | 10/2005 | Clothier | |
| 6,995,345 B2 | 2/2006 | Gorbold | |
| 7,478,749 B2 | 1/2009 | Clothier et al. | |
| 7,489,530 B2 | 2/2009 | Paull | |
| 7,551,011 B2 | 6/2009 | Paull | |
| 7,573,005 B2 | 8/2009 | Clothier | |
| 7,626,463 B2 | 12/2009 | Paull | |
| 7,794,142 B2 | 9/2010 | Clothier et al. | |
| 7,804,045 B2 | 9/2010 | Rosenbloom et al. | |
| 7,816,632 B2 | 10/2010 | Bourke, III et al. | |
| RE42,513 E | 7/2011 | Clothier | |
| 8,192,080 B2 | 6/2012 | Clothier | |
| 8,251,581 B2 | 8/2012 | Clothier et al. | |
| 8,258,441 B2 | 9/2012 | Clothier | |
| 8,286,497 B2 | 10/2012 | Clothier et al. | |
| 8,350,196 B2 | 1/2013 | Buchanan | |
| 8,389,910 B2 | 3/2013 | Bourke, III et al. | |
| 2001/0043450 A1 | 11/2001 | Seale et al. | |
| 2002/0154518 A1 | 10/2002 | Elferich et al. | |
| 2003/0214821 A1 | 11/2003 | Giannopoulos et al. | |
| 2007/0109708 A1 | 5/2007 | Hussman et al. | |
| 2008/0211478 A1 | 9/2008 | Hussman et al. | |
| 2010/0064901 A1 | 3/2010 | Clothier et al. | |
| 2011/0038395 A1 | 2/2011 | Sorkine et al. | |
| 2011/0090937 A1 | 4/2011 | Malyshev et al. | |
| 2012/0205837 A1 | 8/2012 | Clothier | |
| 2012/0230365 A1 | 9/2012 | Clothier | |
| 2012/0250726 A1 | 10/2012 | Sorkine | |
| 2013/0015177 A1 | 1/2013 | Clothier | |

FOREIGN PATENT DOCUMENTS

| | | |
|---|---|---|
| EP | 0 930 808 | 7/1999 |
| GB | 2 124 042 | 2/1984 |
| JP | 59-78496 | 5/1984 |
| JP | 61-96699 | 5/1986 |
| JP | 04-183274 | 6/1992 |
| JP | H06-133476 | 5/1994 |
| JP | 07-153577 | 6/1995 |
| JP | 7-507917 | 8/1995 |
| JP | 8-506927 | 7/1996 |
| JP | 8-214473 | 8/1996 |
| JP | 8-298778 | 11/1996 |
| JP | H08-340285 | 12/1996 |
| JP | H08-340650 | 12/1996 |
| JP | 9-103037 | 4/1997 |
| JP | 09-266081 | 10/1997 |
| JP | 10-012197 | 1/1998 |
| JP | 10-041089 | 2/1998 |
| JP | 10-108391 | 4/1998 |
| JP | H10-174206 | 6/1998 |
| JP | 2001-225129 | 8/1998 |
| JP | H10-215530 | 8/1998 |
| JP | H10-225020 | 8/1998 |
| JP | H10-233235 | 9/1998 |
| JP | H10-258129 | 9/1998 |
| JP | H11-155245 | 7/1999 |
| JP | H11-188113 | 7/1999 |
| JP | 2000-166129 | 8/2000 |
| JP | 2000-270501 | 9/2000 |
| JP | 2000-295796 | 10/2000 |
| JP | 2001-128375 | 8/2001 |
| JP | 2001-238372 | 8/2001 |
| JP | 2002-262567 | 9/2002 |
| JP | 2002-272134 | 9/2002 |
| WO | 94/19919 | 9/1994 |
| WO | 94/22209 | 9/1994 |
| WO | 94/28560 | 12/1994 |
| WO | 96/05648 | 2/1996 |
| WO | 96/17499 | 6/1996 |
| WO | 00/54387 | 9/2000 |
| WO | 00/78678 | 12/2000 |

OTHER PUBLICATIONS

Japanese Office Action, Patent Application No. 2005-304983, Jun. 2, 2008.

Japanese Office Action, Patent Application No. 2005-304983, Apr. 22, 2009.

(56) References Cited

OTHER PUBLICATIONS

Current Control of Quantum Series Resonant Inverter and Application for a DC Motor Drive, Korea Advanced Institute of Science and Technology since 1971, Advisor: Myung Joong Youn by Gun-Woo Moon, Department of Electrical Engineering Korea Advanced Institute of Science and Technology, Dec. 28, 1991.

Malik E. Elbuluk, Member IEEE, George C. Verghese, Member IEEE, and John G. Kassakian, Senior Member, IEEE, Sampled-Data Modeling and Digital Control of Resonant Converters, IEEE Transactions on Power Electronics, vol. 3, No. 3, Jul. 1988.

Gyu B. Joung, Chun T. Rim, and Gyu H. Cho, Integral Cycle Mode Control of the Series Resonant Converter, IEEE Transactions on Power Electronics, vol. 4, No. 1, Jan. 1989.

INDUCTIVELY COUPLED BALLAST CIRCUIT

FIELD OF THE INVENTION

The present invention generally relates to ballasts and more particularly, to an inductively coupled ballast for non-contact power transfer to a secondary circuit or load.

BACKGROUND OF THE INVENTION

Ballasts are commonly used to supply power to a wide variety of electrically powered components. Often ballasts are connected directly to the component (or load), for example, by "permanent" connections, such as wires or soldered leads on a circuit board, or by "removable" connections, such as plugs or other connectors. Direct electrical connections present a number of problems. First, direct electrical connections make it difficult to install and remove the load from the ballast. With permanent connections, the electrical leads must be soldered or otherwise secured directly between the ballast and the load. If the ballast or the load is damaged, replacement is complicated by the permanent connections. Removable connections make separation of the ballast and the load easier, but still require some manual manipulation. Removable connectors are also subject to corrosion and may be inadvertently or unintentionally disconnected, for example, by vibrations. Second, in many environments, direct electrical connections must be insulated from the environment to prevent damage to the circuit. For example, in wet environments, exposed electrical connections are subject to a short circuit. Third, direct electrical connections provide a direct and essentially unimpeded path for electricity to flow between the ballast and the load. As a result, power surges and other potentially damaging abnormalities in one element can be directly transfer to the other, thereby permitting problems in one component to damage or even destroy the other.

To address these and other significant problems, there is an increasing trend to replace conventional direct electrical connections with inductive connections. Inductively coupled systems provide a number of significant advantages over direct connections. First, inductive couplings do not include permanent or removable physical connectors. Instead, the secondary coil of the load (or secondary circuit) simply needs to be placed in the close proximity to the primary coil of the ballast. This greatly simplifies installation and removal of the load. Second, the inductive coupling provide a significant level of isolation between the ballast and the load. This isolation can protect one component from power surges and other potentially damaging abnormalities in the other component.

Unfortunately, conventional inductively coupled ballasts suffer from a number of problems associated primarily with efficiency. To provide maximum efficiency, it is desirable for the circuit to operate at resonance. Conventional ballasts are designed to operate at resonance by carefully selecting the components of the ballast in view of the precise characteristics of the load. Any variation in the load can move the circuit dramatically out of resonance. Accordingly, conventional ballasts require very precise selection of the components of the ballast circuit and secondary circuit. In some applications, the impedance of the secondary circuit will vary over time, thereby changing the resonant frequency of the circuit. For example, in many conventional lighting applications, the impedance of the lamp will vary as the lamp is heated and will also vary over the life of the lamp. As a result of these changes, the efficiency of conventional, fixed-frequency ballasts will vary over time.

Conventional ballast control circuits employ bipolar transistors and saturating transformers to provide power. The ballast control circuits oscillate at frequencies related to the magnetic properties of the materials and winding arrangements of these transformers. Circuits with saturating transformer oscillators produce an output in the category of a square wave, require the transistors of the half bridge to hard-switch under load and require a separate inductor to limit the current through the load. Conventional circuits chop the available power supply voltage, developing voltage spikes at the corners of the square wave as a consequence of the current limiting inductor. Inductive couplings rely on electromagnetic induction to transfer power from a primary coil to a secondary coil. The amount of current induced in the secondary coil is a function of the changes in the magnetic field generated by the primary coil. Accordingly, the amount of current transferred through an inductive coupling is dependent, in part, on the waveform of the current driving the primary. A square waveform has relatively small regions of change and therefore provides relatively inefficient transfer of power.

These and other deficiencies in prior ballasts are addressed by the present invention.

SUMMARY OF THE INVENTION

The present invention discloses an inductively powered ballast circuit having a current sensing circuit that automatically adjusts the frequency of the ballast to maintain operation of the ballast at or near unity power factor.

In one embodiment, the inductively coupled ballast circuit is a self-oscillating half-bridge switching design that operates at high frequencies. In addition, the inductively coupled ballast circuit self-oscillates partly as a function of the current sensing circuit to maintain resonance, uses MOSFET transistors as switching elements, and is designed to accommodate an air-core transformer coupling arrangement.

One embodiment of the inductively coupled ballast circuit includes a control circuit, an oscillator, a driver, a half-bridge switching circuit, and a series resonant tank circuit. The secondary circuit preferably includes a secondary coil and a load. During operation, the control circuit provides electrical signals to the oscillator, which, in turn, provides electrical signals to direct the driver. The driver then causes the half-bridge switching circuit to become energized. The half-bridge switching circuit energizes the series resonant tank circuit, which includes a primary coil. Once the series resonant tank circuit, and consequently the primary coil, is energized, the secondary coil becomes inductively energized, thereby providing power to the load.

In one embodiment, the resonant frequency for the inductively coupled ballast circuit is about 100 kHz. In addition, the secondary circuit preferably resonates at about 100 kHz as well. The resonant frequency of operation can be adjusted up or down by the control unit to accommodate for convenient component selection. In addition, selection of the resonant frequency is a function of the component selection in the series resonant tank and the characteristics of the secondary circuit.

An interesting feature of the inductively coupled ballast circuit is the inductive coupling. The series resonant tank circuit includes an inductive coupler. In one embodiment, the inductive coupler is positioned adjacent the secondary coil with an air gap therebetween to form an air core transformer.

When voltage is applied to the inductive coupler, magnetic flux in the air gap induces voltage in the secondary coil thereby energizing the secondary load.

Another interesting feature of the inductively coupled ballast circuit involves the air gap of one embodiment. The air gap is the distance between the inductive coupler and the secondary coil. The air gap may be selected to provide a current limiting function. In addition, the air gap provides a magnetic flux path for inducing sufficient voltage in the secondary coil to establish and maintain an operating point for the secondary load.

Yet another interesting feature involves the frequency of operation of the inductively coupled ballast circuit. Both the series resonant tank and the secondary load may be tuned by proper selection of components to operate at a similar resonant frequency. In addition, impedance matching between the series resonant tank and the secondary load may occur at the resonant frequency. Accordingly, power transfer from the inductive coupler to the secondary coil may be optimized at a resonant frequency to maximize power efficiency.

Still another interesting feature involves self-oscillation of the inductively coupled ballast circuit with the oscillator. The oscillator may include feedback control for monitoring the series resonance tank. The feedback control may allow the oscillator to adjust the frequency to minimize reflected impedance from the secondary circuit. Adjusting the frequency to maintain resonance minimizes the reflected impedance and maintains optimum power transfer as the impedance of the secondary circuit varies.

In another aspect, the present invention preferably includes a current limit circuit that monitors the ballast circuit and disables the ballast circuit if the current to the primary exceeds a desired threshold. The current limit circuit protects both the load and the ballast circuit from excessive current. The current limit circuit is preferably latched to keep the ballast circuit disabled until reset, for example, by a manual reset switch.

In an alternative embodiment, the current limit circuit may be configured to disengage the ballast circuit if the current falls outside of a desired operating range. This embodiment is particularly useful in application where the load may be damaged or function improperly when operating under low current.

These and other features and advantages of the invention will become apparent upon consideration of the following detailed description of the presently preferred embodiments of the invention, viewed in conjunction with the appended drawings.

DETAILED DESCRIPTION OF THE DRAWINGS

FIG. 1 is a perspective view of a main housing of the water treatment system with its top shroud removed and a filter assembly and the ultraviolet lamp assembly removed from the base unit.

FIGS. 2A-C are exploded perspective views of major components of the water treatment system.

DETAILED DESCRIPTION OF THE ILLUSTRATED EMBODIMENT OF THE INVENTION

The present invention is directed to an inductively coupled ballast circuit that is capable of providing power to a wide variety of electrically powered components in numerous applications. For purposes of disclosure, embodiments of the ballast circuit will be described in connection with a water treatment system, and more specifically in connection with the powering of an ultraviolet lamp in a water treatment system. Although described in connection with this particular application, the present invention is well-suited for use in providing power to other types of lamps, such as incandescent, fluorescent and halogen lamps used in numerous lighting applications, such as indoor and outdoor light fixtures, desk lamps, outdoor signage, decorative lighting, automotive lighting, underwater lighting, intrinsically safe lighting, and landscape lighting, to name only a few lighting configurations and applications. The present invention is also well suited for providing power to non-lighting components, such as integrated battery chargers in various electronic components, including cell phones, personal digital assistants and the like.

Figure 1:
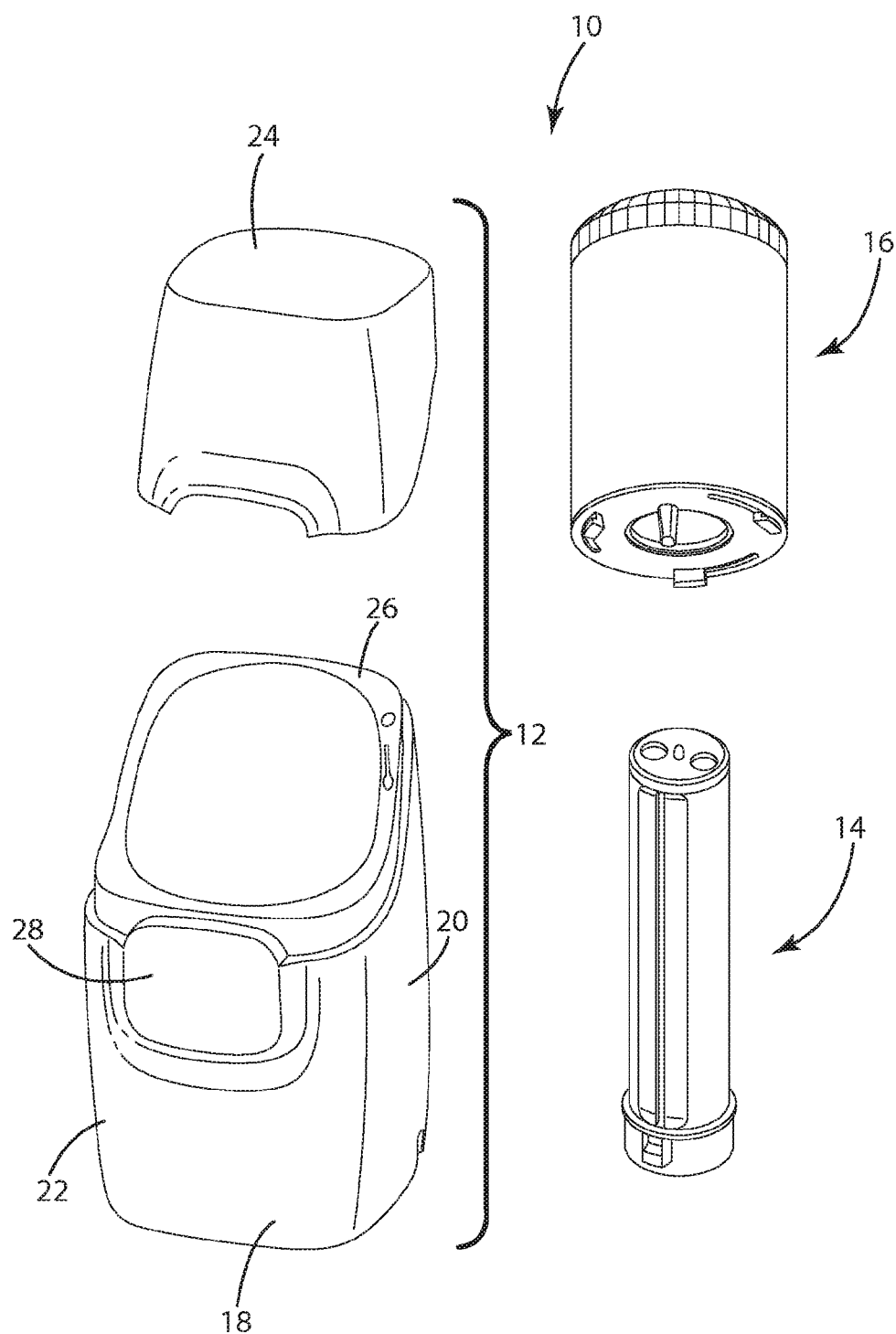

Referring to FIG. 1, the present invention, as used in the illustrated embodiment, discloses an electronic control system for a water treatment system 10 that generally uses carbon-based filters and ultraviolet light to purify water. In order to appreciate the present invention, it is helpful to have a general background of the mechanical aspects of water treatment system 10 for which this illustrated embodiment was intended. Water treatment system 10 includes a main housing 12, a replaceable ultraviolet lamp assembly 14 and a filter assembly 16. The ultraviolet lamp assembly 14 and the filter assembly 16 are removable and replaceable from the main housing 12. The main housing 12 includes a bottom shroud 18, a back shroud 20, a front shroud 22, a top shroud 24 and an inner sleeve shroud 26. A lens 28 accommodates a display 106 (see FIG. 3) so that information may be displayed about the status of the water treatment system 10 through the display 106. To assemble the water treatment system 10, the ultraviolet lamp assembly 14 is securely mounted to the main housing 12 and thereafter the filter assembly 16 is mounted over the ultraviolet lamp assembly 14 and to the main housing 12.

As those skilled in the art would recognize, the replaceable ultraviolet lamp assembly 14 may be made in such a manner that the ultraviolet lamp assembly 14 may not be replaceable. In addition, those skilled in the art would recognize that the replaceable ultraviolet lamp assembly 14 may be interchanged with several different types of electromagnetic radiation emitting assemblies. As such, the present invention should not be construed to cover only systems that use ultraviolet lamp assemblies and those skilled in the art should recognize that the disclosure of the ultraviolet lamp assembly 14 represents only one embodiment of the present invention.

Figure 2:
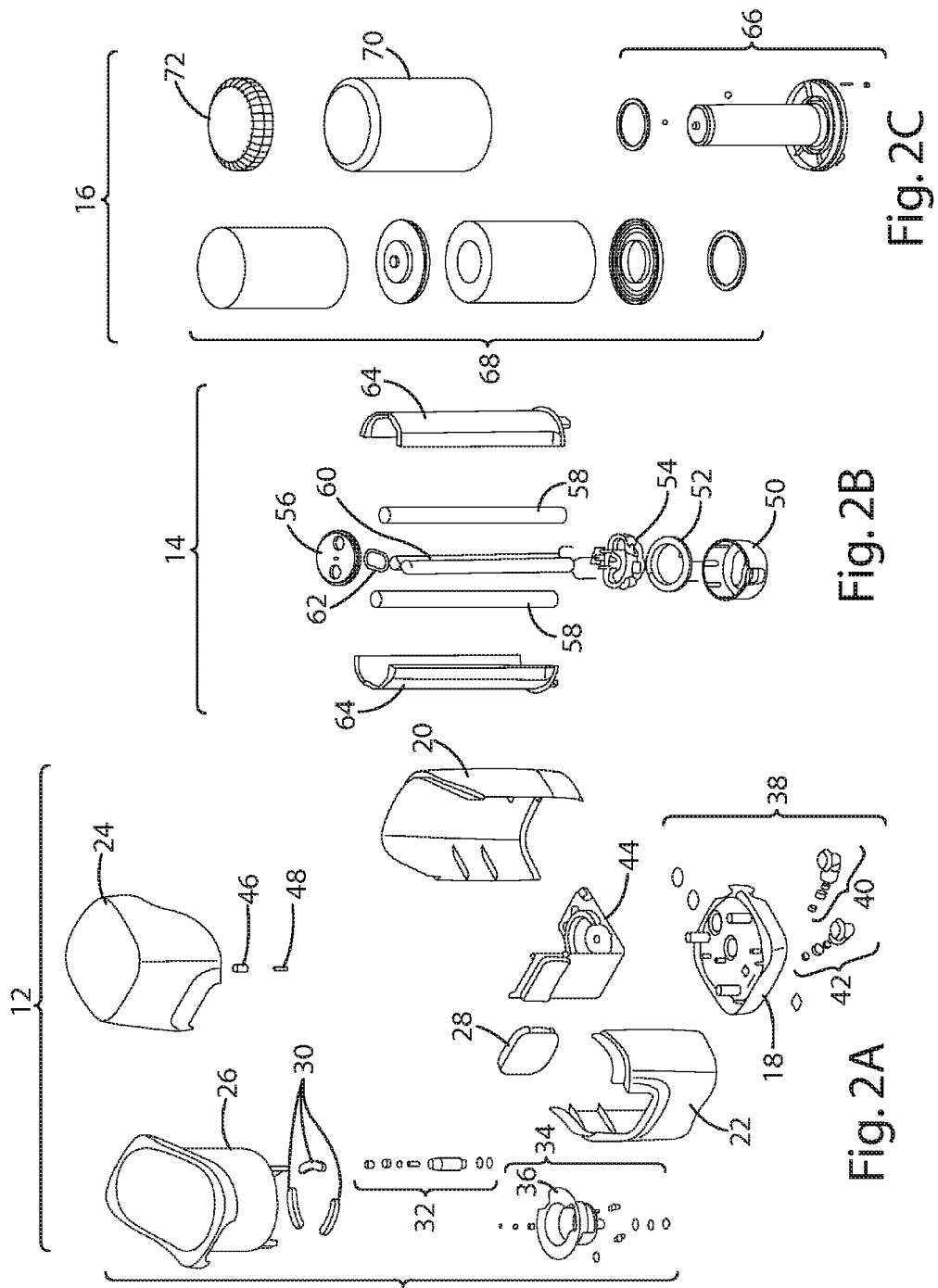

Referring to FIGS. 2A-C, the major mechanical components of the water treatment system 10 are shown in perspective view, as relevant to the present invention. As illustrated in FIG. 2A, the inner sleeve shroud 26 includes a plurality of inner sleeve covers 30, an inlet valve assembly 32 and an outlet cup assembly 34 with an outlet cup 36. A bottom shroud assembly 38 is further disclosed that includes the bottom shroud 18 along with an inlet assembly 40 and an outlet assembly 42. An electronics assembly 44 fits securely in the bottom shroud 18, the details of which will be set forth below in detail. These components are securely mounted to the bottom shroud 18, the back shroud 20, the front shroud 22, the top shroud 24, the inner sleeve shroud 26 and the lens 28 when the water treatment system 10 is fully assembled. A magnet holder 46 and a magnet 48 are also housed in the top shroud 24 in the illustrated embodiment.

Referring to FIG. 2B, the ultraviolet lamp assembly 14 generally includes a base subassembly 50, a secondary coil 52, a bottom support subassembly 54, a top support assembly 56, a pair of quartz sleeves 58, an ultraviolet lamp 60, an O-ring 62 and a pair of cooperating enclosure reflector subassemblies 64. Generally speaking, the secondary coil 52, the bottom support subassembly 54 and the enclosure reflector subassemblies 64 are connected with the base subassembly 50. The enclosure reflector subassemblies 64 house the pair of quartz tubes 58, the ultraviolet lamp 60 and the O-ring 62. The top support assembly 56 fits securely over the top of the enclosure reflector assemblies 64 when the ultraviolet lamp assembly 14 is fully assembled.

As illustrated in FIG. 2C, the filter assembly 16 generally includes a base assembly 66, a filter block assembly 68, a filter housing 70 and an elastomeric filter-housing grip 72. Generally speaking, the filter block assembly 68 fits over the base assembly 66 which, in turn, is encapsulated by the filter housing 70. The filter housing grip 72 fits over the top of the filter housing 70, thereby providing a better grip for removing the filter housing 70. The filter assembly 16 filters a flow of water by directing the flow through the filter block assembly 68 before being directed to the ultraviolet lamp assembly 14.

Figure 3:
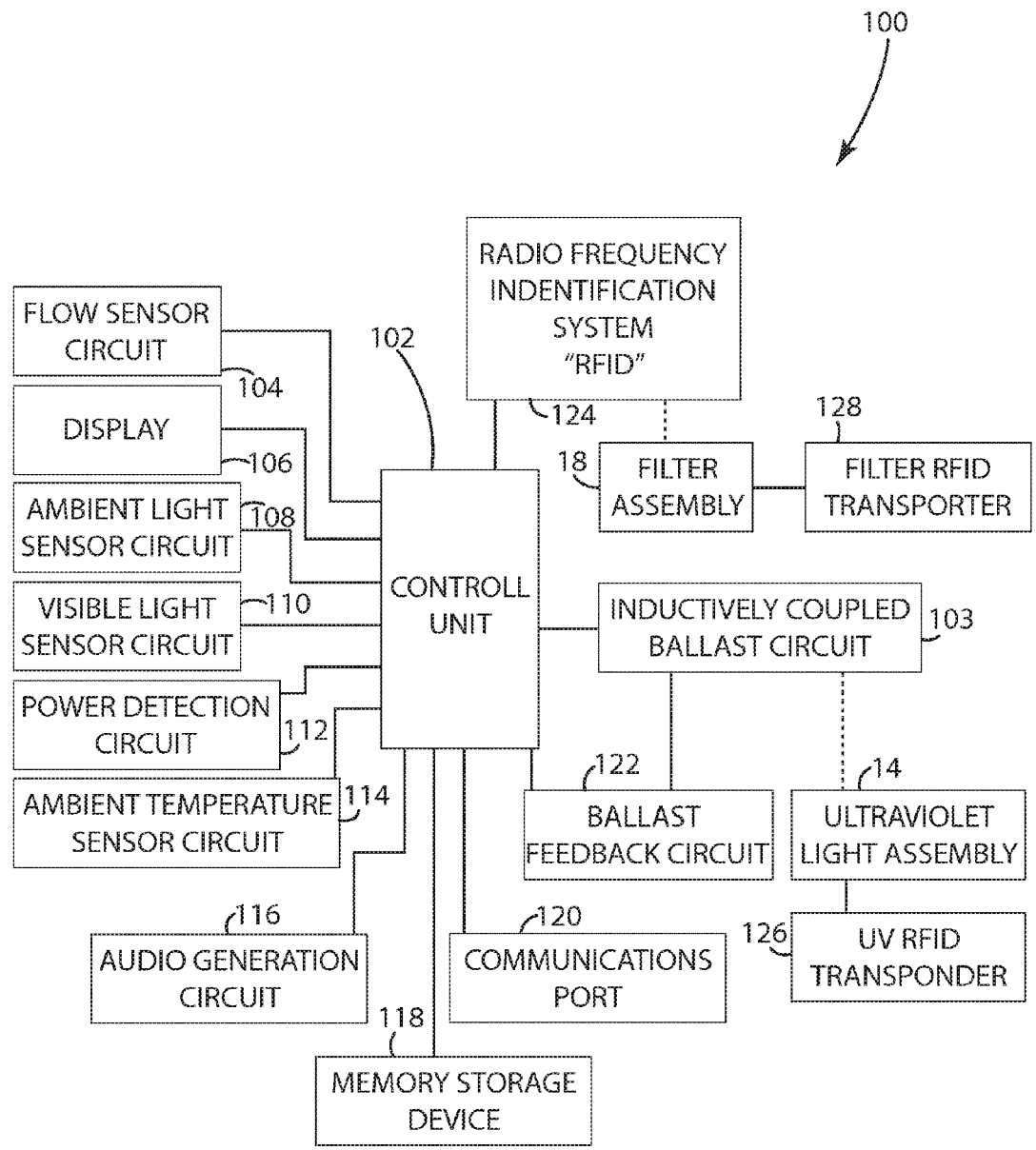
FIG. 3 depicts a block diagram of the major circuits and assemblies of the water treatment system.
Figure 4:
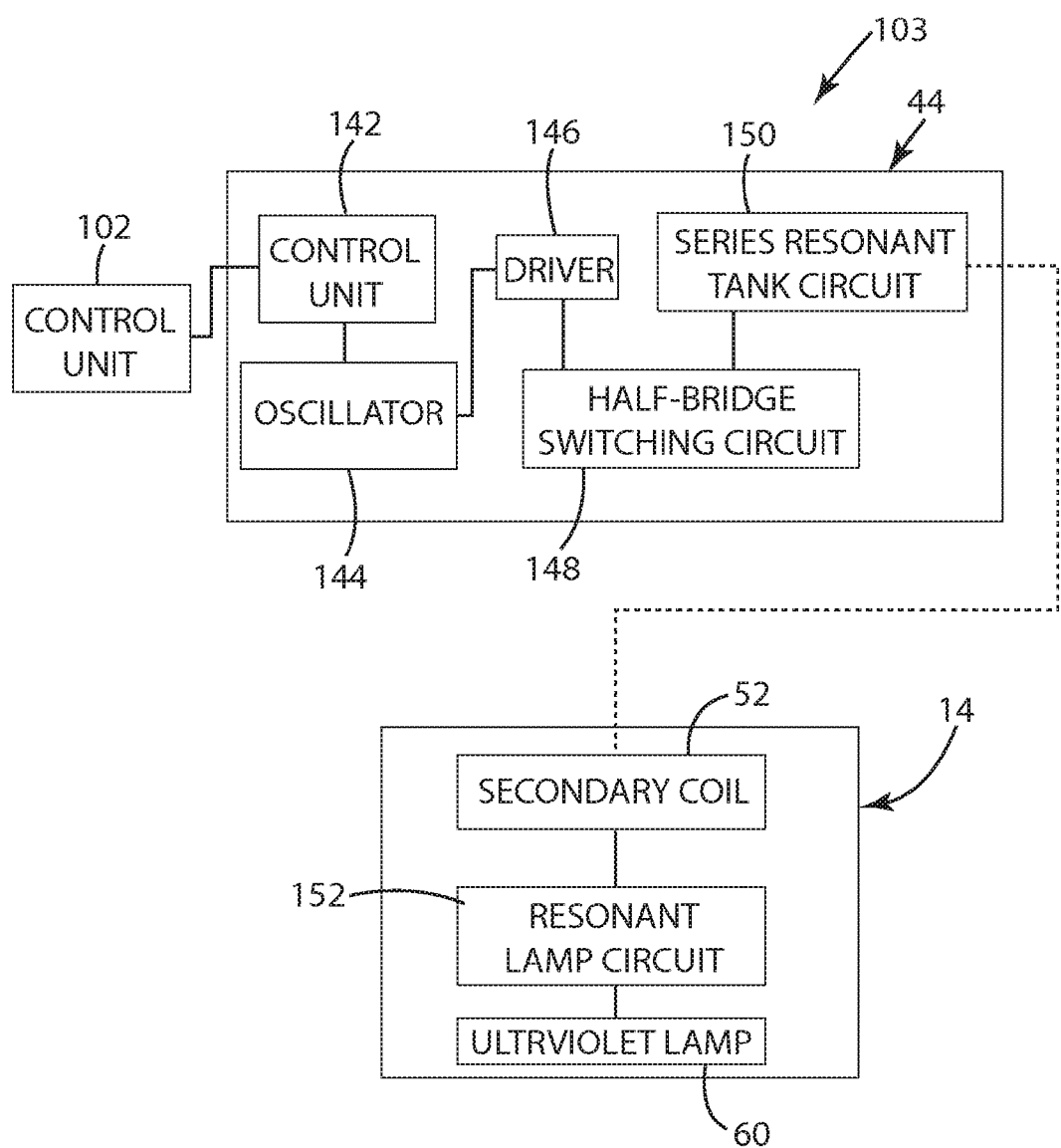
FIG. 4 depicts a block diagram of the inductively coupled ballast circuit.

FIG. 3 illustrates an electronic control system 100 for the water treatment system 10 generally described above. In the illustrated embodiment, the water treatment system 10 is controlled by a control unit 102, which is preferably a microprocessor. As illustrated in FIG. 4, the control unit 102 is electrically connected with the inductively coupled ballast circuit 103 of the present invention. The ballast circuit 103 includes the ultraviolet lamp assembly 14 and electronic assembly 44, which are inductively coupled as illustrated by the dotted line in FIG. 4. This control unit 102 is also electrically connected to the ultraviolet lamp assembly 14 through two-way wireless communication, as will be set forth in greater detail below. During operation, the control unit 102 is capable of generating a predetermined electric signal that is directed to the inductively coupled ballast circuit 103, which instantaneously energizes the lamp assembly 14 which, in turn, provides high-intensity ultraviolet light that treats the flow of water.

In the illustrated embodiment, the control unit 102 is also electrically connected with a flow sensor circuit 104, a display 106, an ambient light sensor circuit 108, a visible light sensor circuit 110, a power detection circuit 112, an ambient temperature sensor circuit 114, an audio generation circuit 116, a memory storage device 118, a communications port 120, a ballast feedback circuit 122 and a radio frequency identification system 124. As further illustrated in FIG. 3, an ultraviolet light radio frequency identification transponder 126 is connected with the ultraviolet lamp assembly 14 and a filter radio frequency identification transponder 128 is connected with the filter assembly 16. The ultraviolet radio frequency identification transponder 126 and the filter radio frequency identification transponder 128 communicate with the radio frequency identification system 124 using two-way wireless communication, as will be set forth in greater detail below.

Generally speaking, the flow sensor circuit 104 is used by the control unit 102 to determine when water or fluid is flowing and to keep track of the volume of water or fluid that is being processed by the water treatment system 10. The display 106 is driven by the control unit 102 and is used to display information about the status of the water treatment system 10. Several different types of displays are known in the art and may be used in the present invention; however, the preferred display is a vacuum florescent display. The ambient light sensor circuit 108 measures the amount of ambient light and, in turn, provides electrical signals to the control unit 102 so that it can adjust the intensity of the display 106 accordingly.

The visible light sensor circuit 110 provides the control unit 102 with electrical signals related to the intensity level of the light that is being emitted by the ultraviolet lamp assembly 14. This is important because these signals allow the control unit 102 to increase or decrease the intensity of the electromagnetic radiation being emitted by the ultraviolet lamp assembly 14. Those skilled in the art would recognize that the visible light sensor circuit 110 may be interchanged with various electromagnetic radiation sensor circuits that are capable of sensing the intensity of electromagnetic radiation that is emitted from various electromagnetic radiation emitting devices that may be used in the present invention.

The power detection circuit 112 provides the control unit 102 with electrical signals that indicate the presence or absence of power to the water treatment system 10. Power is provided to the water treatment system 10 from an external power source, such as a conventional power outlet. Those skilled in the art would recognize that several circuits exist that monitor external power sources and provide corresponding electrical signals in response to losses of power.

The ambient temperature sensor circuit 114 measures the ambient temperature of the atmosphere so that the water treatment system 10 can maintain a temperature level above freezing or some other predetermined temperature setting. The control unit 102 can energize the ultraviolet lamp 60 to generate heat if necessary. The audio generation circuit 116 is used by the control unit 102 to generate audible enunciations. The audible enunciations typically occur during predetermined system states that are experienced by the water treatment system 10. These predetermined system states are recognized by the control unit 102 which, in turn, activates the audio generation circuit 116 to create the audible enunciation.

As previously set forth, the memory storage device 118 is also electrically connected with the control unit 102. The memory storage device 118 is used to store various data values related to the water treatment system 10 and its related components. In the illustrated embodiment, the memory storage device 118 is an EEPROM or some other equivalent storage device. Those skilled in the art would recognize that various memory storage devices are available that could be used in the present invention.

The communications port 120 is also electrically connected with the control unit 102, which provides the water treatment system 10 with the ability to conduct bi-directional communication between the control unit 102 and a peripheral device, such as a personal computer or hand-held monitoring device. In the illustrated embodiment, the communications port 120 uses the RS-232 communication platform to communicate with the peripheral device. The communications port 120 may also be connected with the ultraviolet lamp assembly 14 and the filter assembly 16 to monitor and control various operational characteristics of these devices in other embodiments. However, in the illustrated embodiment, the radio frequency identification system 124 is used to report information to the control unit 102 about the ultraviolet lamp assembly 14 and the filter assembly 16.

In the embodiment depicted in FIG. 3, the radio frequency identification system 124 uses signals from the ultraviolet light radio frequency identification transponder 126 and the filter radio frequency identification transponder 128 to report various information to the control unit 102. During operation, the ultraviolet light radio frequency identification transponder 126 and the filter radio frequency identification transponder 128 communicate with the radio frequency identification system 124 using wireless communication. Since the ultraviolet lamp assembly 14 and the filter assembly 16 are designed to be replaceable at the end of its useful life, each ultraviolet lamp assembly 14 and filter assembly 16 contains a transponder 126, 128 that stores information specific to each device. Those skilled in the art would recognize that the ultraviolet light radio frequency transponder could be used in conjunction with other electromagnetic radiation emitting devices or assemblies. The radio frequency identification system 124 is set forth in greater detail below.

Referring to FIG. 4, in the illustrated embodiment of the invention, the ultraviolet lamp assembly 14 is energized by the inductively coupled ballast circuit 103 that is electrically connected with the control unit 102. In the illustrated embodiment, the inductively coupled ballast circuit 103 is a self-oscillating, half-bridge switching design that operates at high frequencies. The inductively coupled ballast circuit 103 self-oscillates once resonance is achieved, uses MOSFET transistors as switching elements, and is designed to accommodate an air-core transformer coupling arrangement, which simplifies the design of the ultraviolet lamp assembly 14. The ultraviolet lamp assembly 14 or other electromagnetic radiation emitting assemblies may be readily replaced because of the air-core transformer coupling arrangement created by the inductively coupled ballast circuit 103.

As illustrated in FIG. 4, the inductively coupled ballast circuit 103 of the described embodiment generally includes a control circuit 142, an oscillator 144, a driver 146, a half-bridge switching circuit 148, and a series resonant tank circuit 150. The ultraviolet lamp assembly 14 generally includes the secondary coil 52 (see FIG. 2), a resonant lamp circuit 152 and the ultraviolet lamp 60. The oscillator 144 is electrically connected with the control unit 102, which energizes the oscillator 144 by providing electric signals to the control circuit 142. During operation, the oscillator 144 provides electrical signals to direct the driver 146, which then causes the half-bridge switching circuit 148 to become energized. The half-bridge switching circuit 148 energizes the series resonant tank circuit 150 that, in turn, inductively energizes the ultraviolet lamp 60 in the ultraviolet lamp assembly 14.

As noted above and as further illustrated in FIG. 4, the ultraviolet lamp assembly 14 includes the secondary coil 52, the resonant lamp circuit 152 and the ultraviolet lamp 60 while the electronic assembly 44 houses the control circuit 142, the oscillator 144, the driver 146, the half-bridge switching circuit 148 and the series resonant tank circuit 150. As previously set forth, once the series resonant tank circuit 150 is energized, the secondary coil 52 in the ultraviolet lamp assembly 14 becomes inductively energized as illustrated by the dotted line in FIG. 4. In the illustrated embodiment, the resonant frequency for the ballast circuit 103 is about 100 kHz. In addition, the ultraviolet lamp assembly 14 resonates at about 100 kHz as well. The frequency of operation may be varied to maintain resonance of the series resonant tank circuit 150 and the ultraviolet lamp assembly 14 as discussed in detail below. As known to those skilled in the art, the resonant frequency may be any desired frequency selected as a function of the component selection in the series resonant tank circuit 150 and the ultraviolet lamp assembly 14.

Figure 5:
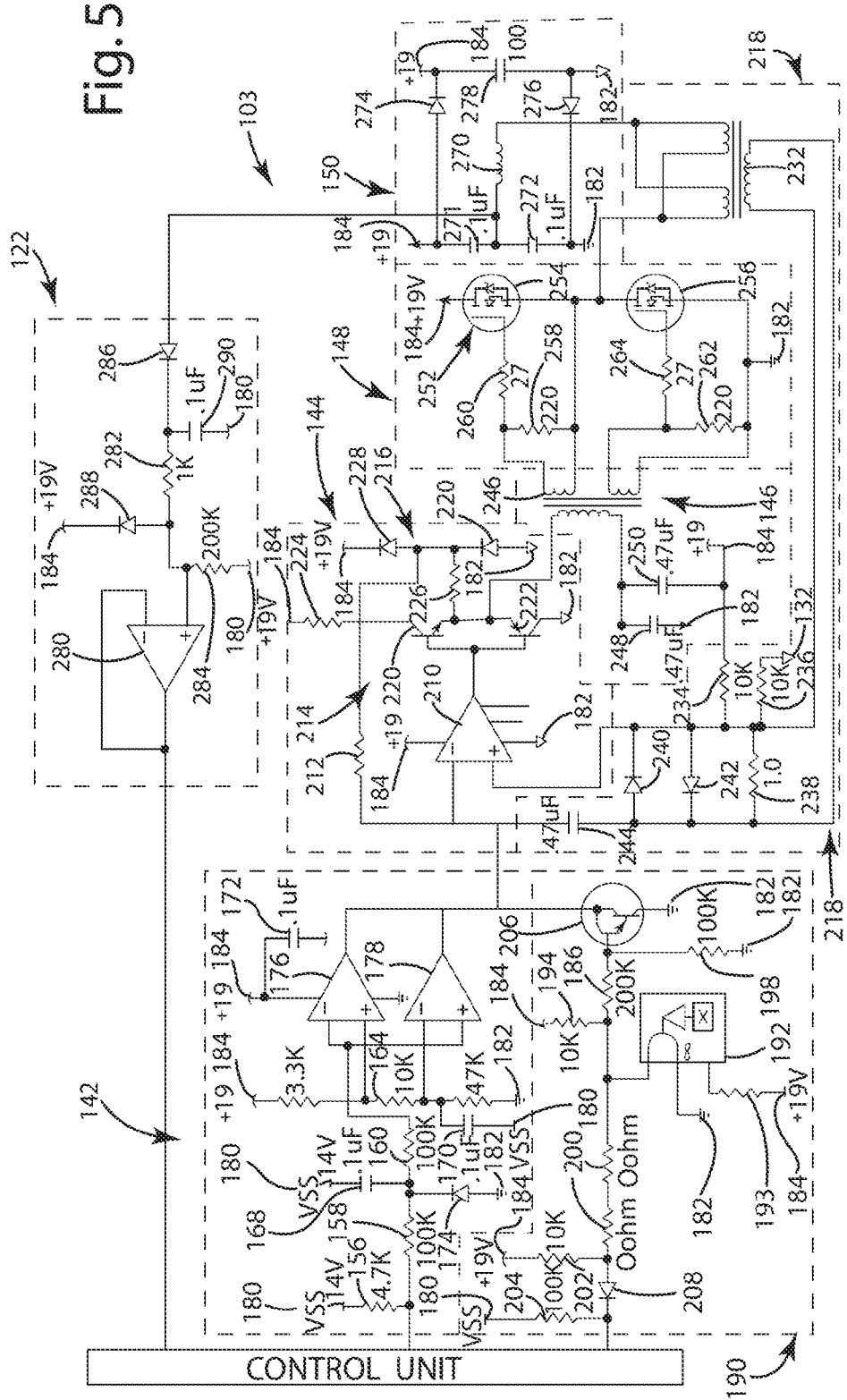
FIG. 5 is an electrical circuit schematic of a portion of the inductively coupled ballast circuit, the ballast feedback circuit and the interlock circuit.

Referring to FIG. 5, the control circuit 142 is electrically connected with the control unit 102 and the oscillator 144. The control circuit 142 includes a plurality of resistors 156, 158, 160, 162, 164, 166, a plurality of capacitors 168, 170 172, a diode 174, a first operational amplifier 176 and a second operational amplifier 178. As illustrated, resistor 156 is connected with a first direct current ("DC") power source 180, the output of the control unit 102 and resistor 158. Resistor 158 is further connected with diode 174, resistor 160 and capacitor 168. The first DC power source 180 is connected with capacitor 168, which is also connected with diode 174. Diode 174 is further connected with a ground connection 182, as those skilled in the art would recognize. Resistor 160 is connected with the negative input of operational amplifier 176 and the positive input of operational amplifier 178 to complete the current path from the control unit 102 to the operational amplifiers 176, 178.

Referring once again to the control circuit 142 depicted in FIG. 5, resistor 162 is connected with a second DC power source 184 and in series with resistors 164 and 166. Resistor 166 is connected with the ground connection 182 and capacitor 170, which is, in turn, connected with the first DC power source 180 and resistor 164. The positive input of operational amplifier 176 is electrically connected between resistors 162 and 164, which provides a DC reference voltage to operational amplifier 176 during operation. The negative input of operational amplifier 178 is electrically connected between resistors 164 and 166, which provides a DC reference voltage to operational amplifier 178 during operation. The output of operational amplifiers 176 and 178 is connected with the oscillator 144, as set forth in detail below.

During operation, the control circuit 142 turns the oscillator 144 on and off based on input from the control circuit 102 and the magnetic interlock sensor 192, as described in more detail below. The control circuit 142 receives electrical signals from the control unit 102 and, in turn, acts as a window comparator that only switches the oscillator 144 on when the input voltage produced by the control unit 102 is within a certain voltage window. The preferred signal from the control unit 102 is an AC signal that, together with its duty cycle, allows the control unit 102 to turn the ultraviolet lamp 60 on and off through the remaining components of the inductively coupled ballast circuit 103, as will be set forth below. The control circuit 142 also prevents false triggering and allows positive control if the control unit 102 fails.

As illustrated in FIG. 5, the first DC power source 180 and the second DC power source 184 provide power to the circuits depicted in FIG. 5. Those skilled in the art of electronics would recognize that DC power supply circuits are well known in the art and beyond the scope of the present invention. For the purposes of the present invention, it is important to note that such circuits exist and are capable of being designed to produce various DC voltage values from a given AC or DC power source. In the illustrated embodiment, a +14VDC and a +19VDC signal is used, as indicated throughout the figures. Those skilled in the art would recognize that the circuits disclosed in FIG. 5 could be designed to operate on different DC voltage levels and that these values should not be construed as a limitation on the present invention. In another embodiment, 300VDC is used to supply power to the half-bridge switching circuit 148 to optimize power transfer.

In the embodiment depicted in FIG. 5, the output of the control circuit 142 is connected with an interlock circuit 190 to prevent the ultraviolet lamp 60 from becoming energized if the water treatment system 10 is not properly assembled. The interlock circuit 190 includes a magnetic interlock sensor 192, a plurality of resistors 193, 194, 196, 198, 200, 202, 204, a transistor 206 and a diode 208. Referring to FIG. 1, in the illustrated embodiment, the magnetic interlock sensor 192 is positioned so that if the top shroud 24 is not securely positioned on the inner sleeve shroud 26, the water treatment system 10 will not energize the ultraviolet lamp 60. However, those skilled in the art would recognize that the magnetic interlock sensor 192 may be placed in other convenient places of the water treatment system 10 as well.

Referring to FIG. 5, the magnetic interlock circuit 190 operates by directing the output of the control circuit 142 to the ground connection 182, through transistor 206, if the magnetic interlock sensor 192 detects that the water treatment system 10 is not assembled properly, as set forth above. As those skilled in the art would recognize, if the water treatment system 10 is not assembled properly, the output of the magnetic interlock sensor 192 causes the current flowing through resistors 194, 196 and 198 to energize the gate of transistor 206, which thereby shorts the output signal of the control circuit 142 to the ground connection 182. The magnetic interlock sensor 192 is powered by the second DC power source 184 through resistor 193 and is also connected with the ground connection 182. In addition, the magnetic interlock sensor 192 sends a signal to the control unit 102, through the combination of resistors 200, 202 and 204, diode 208, first DC power source 180 and second DC power source 184. This signal also allows the control unit 102 to determine when the water treatment assembly 10 is not assembled properly. To that end, the interlock circuit 190 provides two methods of ensuring that the ultraviolet lamp 60 is not energized if the water treatment system 10 is not assembled properly. The magnetic interlock is not necessary for the operation of the present invention.

Referring once again to FIG. 5, the oscillator 144 provides electrical signals that energize the driver 146 while the water treatment system 10 is treating a flow of water. The oscillator 144 begins operating immediately once an electrical signal is sent from the control unit 102, through control circuit 142, as set forth above. As readily apparent, the oscillator 144 may also be controlled by any other mechanism capable of activating and deactivating the oscillator 144. The illustrated oscillator 144 comprises an operational amplifier 210, a linear bias resistor 212, a buffer circuit 214, a buffer feedback protect circuit 216 and a current sensing circuit 218. During operation, the operational amplifier 210 receives input signals from the control circuit 142, the linear bias resistor 212 and the current sensing circuit 218. The operational amplifier 210 is also connected with the second DC power source 184 and the ground connection 182, which energizes the operational amplifier 210.

As illustrated in FIG. 5, the illustrated buffer circuit 214 comprises a first transistor 220, a second transistor 222 and a pair of resistors 224, 226. The output of operational amplifier 210 is connected with the gates of transistors 220, 222, thereby controlling operation of transistors 220, 222. The second DC power source 184 is connected with resistor 224, which is also connected with collector of transistor 220. The emitter of transistor 220 is connected with resistor 226, the emitter of transistor 222 and the input of the driver 146. The collector of transistor 222 is connected with ground connection 182. During operation, the buffer circuit 214 buffers the output signal from the operational amplifier 210 and prevents load changes from pulling the frequency of oscillation. In addition, the buffer circuit 214 increases the effective gain of the inductively coupled ballast circuit 103, which helps ensure a quick start of the oscillator 144.

The buffer feedback protect circuit 216 comprises a pair of diodes 228, 230 that are electrically connected with the output of the buffer circuit 214 by resistor 226. As illustrated in FIG. 5, the second DC power source 184 is connected with the cathode of diode 228. The anode of diode 228 and the cathode of diode 220 are connected with resistor 226 and the linear bias resistor 212. The linear bias resistor 212 provides bias feedback signals to the negative input of operational amplifier 210. In addition, the anode of diode 230 is connected with ground connection 182, which completes the buffer feedback protect circuit 216. The buffer feedback circuit 216 protects the buffer circuit 214 from drain to gate Miller-effect feedback during operation of the water treatment system 10.

As illustrated in FIG. 5, the current sensing circuit 218 includes a first multi-winding transformer 232, a plurality of resistors 234, 236, 238, a pair of diodes 240, 242, and a capacitor 244. The transformer 232 preferably includes a primary having two windings that are connected in parallel between the output of the half-bridge switching circuit 148 and the input of the series resonant tank circuit 150 as illustrated in FIG. 5. The transformer 232 preferably includes a primary with two windings connected in parallel rather than a single winding to reduce the total reactance on the primary side of the transformer, thereby reducing the reactive impact of the transformer 232 on the tank circuit 150. In other applications, the primary side of the transformer may be divided into a different number of windings. For example, the transformer 232 may include only a single winding where reduction of the reactive impact of the transformer is not important or may include three or more windings where even further reduction of the reactive impact of the transformer 232 is desired.

The first lead of the secondary coil of transformer 232 is electrically connected with resistors 234, 236, 238, the diodes 240, 242 and the positive input of the operational amplifier 210. The second lead of the secondary coil of the transformer 232 is connected with resistor 238, the cathode of diode 242, the anode of diode 240 and capacitor 244. As such, resistor 238 and diodes 242, 244 are connected in parallel with the secondary winding of transformer 232, as illustrated in FIG. 5. Capacitor 244 is also electrically connected with the negative input of operational amplifier 210. In addition, resistor 234 is connected with the second DC power source 184 and resistor 236 is connected with the ground connection 182. Resistors 234, 236 and 238 protect the operational amplifier 210 from current overload and diodes 240, 242 clip the feedback signal that is sent to the input of the operational amplifier 210.

During operation, the oscillator 144 receives signals from the control circuit 142 that charge capacitor 244, which, in turn, sends an electrical signal to the negative input of the operational amplifier 210. The output of the operational amplifier 210 is electrically connected to the driver 146 through the buffer circuit 214. As described in more detail below, the driver 146 energizes the half-bridge switching circuit 148, which in turn provides power to the tank circuit 150 ultimately powering inductive coupler 270. As illustrated in FIG. 5, the transformer 232 is connected in the current path between the half-bridge switching circuit 148 and the tank circuit 150. The transformer 232 sends electrical signals back through resistors 234, 236 and 238, which limit the current, to the inputs of the operational amplifier 210 to provide a current sensing feedback. As described in more detail below, the current sensing feedback provided by transformer 232 allows the oscillator 144 to self-resonate despite changes in the load. The inductively coupled ballast circuit 103 remains oscillating until the control unit 102 shuts the water treatment system 10 down or transistor 206 of the interlock circuit 190 pulls the input to the oscillator 144 low.

Figure 15:
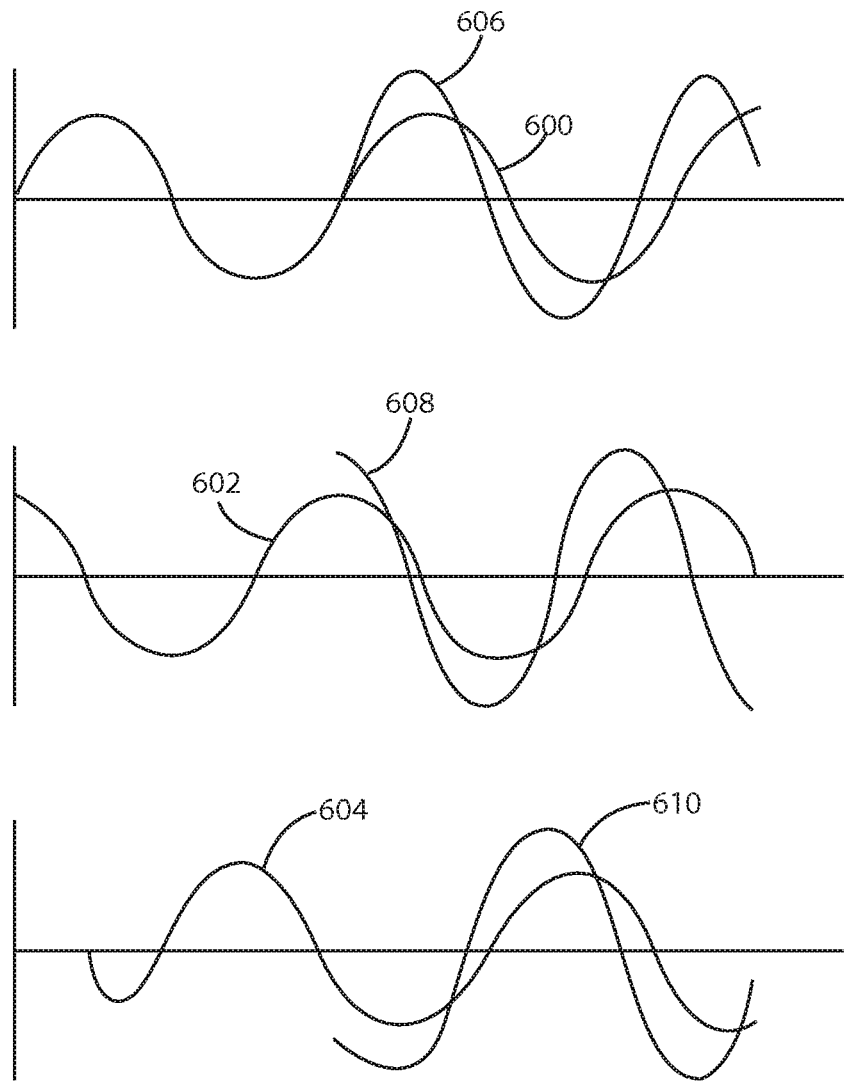
FIG. 15 is a plurality of waveforms representing operation of the current sensing circuit.
Figure 17:
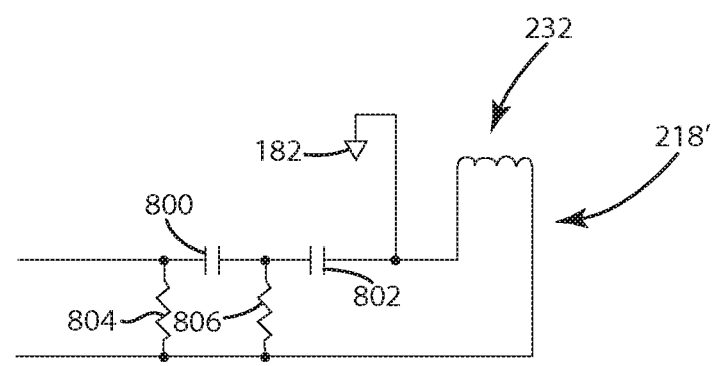
FIG. 17 is an electrical circuit schematic of a portion of an alternative current feedback circuit.

More specifically, the current sensing circuit 218 provides feedback to the operational amplifier 210 that controls the timing of the oscillator 144 so that the oscillator 144 does not impair the tank circuit's 150 inherent tendency to oscillate at resonant frequency. In general, the current in the series resonant tank circuit 150 flows through the primary coils of transformer 232, thereby inducing a voltage in the secondary coil of transformer 232. The AC signal generated by the transformer 232 is superimposed upon a DC reference voltage set by resistors 234 and 236. The operational amplifier 210 is preferably a conventional difference operational amplifier providing an output based, in part, on the difference between the amplitude of the signal on the positive lead and the amplitude of the signal of the negative. Accordingly, the output of the operational amplifier 210 oscillates above and below the reference voltage in accordance with the oscillating signal of the current feedback circuit. The operational amplifier 210 is preferably alternately driven between saturation and cutoff, thereby providing a quasi-square wave output. When the output of the operational amplifier 210 exceeds the reference signal, transistor 220 is driven to "on," while transistor 222 is driven to "off," thereby charging capacitor 248 and discharging capacitor 250. When the output of the operational amplifier 210 falls below the reference signal, transistor 222 is driven to "on" while transistor 220 is driven to "off," thereby discharging capacitor 248 and charging capacitor 250. This alternating charging/discharging of capacitors 248 and 250 results in an alternating signal being applied to the primary coil of the driver 146, as described in more detail below. The frequency shifting (or resonance seeking) operation of the circuit is described in more detail with reference to FIG. 15. In this illustration, the current in the inductive coupler 270 is represented by waveform 600, the voltage in the current transformer 232 is represented by waveform 602 and the current feedback signal is represented by waveform 604 (shown without clipping of diodes 240 and 242). As noted above, the operational amplifier 210 is alternately driven between saturation and cutoff with a transition period interposed between the saturation and cutoff portions of the waveform. The length of the transition period is dictated by the slope of the current feedback signal. The timing of the operational amplifier 210 is dependent on the length of the transition period. By varying the length of the transition period, the timing of the transitions in the operational amplifier 210 output signal is controlled. This shift in timing is perpetuated through the driver 146 and half-bridge switching circuit 148 having the affect of varying the frequency and also possibly the amplitude of the signal in the tank circuit 150. The altered signal in the tank circuit 150 is reflected into the current feedback signal by the current transformer 232 to perpetuate the frequency shift. When the load on the secondary coil 52 increases, a corresponding increase occurs in the amplitude of the current in the tank circuit 150. This increased signal is represented by waveform 606 in FIG. 15. The increased signal in the tank circuit 150 results in a corresponding increase in the voltage in the current transformer 232. The increased voltage in the current transformer 232 is represented by waveform 608. The increased voltage in the current transformer 232 finally results in an increase in the amplitude of the current feedback signal, represented by waveform 610 (shown without clipping of diodes 240 and 242). The increased current feedback signal has a greater slope at the zero crossings and therefore causes the operational amplifier 210 to transition from one state to the other sooner in time. This in turn causes the transistors 220 and 222 to switch sooner in time and the AC signal applied to the driver 146 to alternate sooner in time. Ultimately, there is a corresponding shift in the timing of the signals applied to the tank circuit 150 by the half-bridge switching circuit 148. The shift in timing of the signals applied by the half-bridge switching circuit 148 has the effect of increasing the frequency and possibly the amplitude of the inherent oscillating signal in the tank circuit 150, thereby shifting, or "truncating," the timing of the signal in the tank circuit 150. The truncated signal in the tank circuit 150 is reflected into the current sensing circuit 218. This varies the current feedback signal applied to the operational amplifier 210, thereby perpetuating the frequency shift and effecting an increase in the frequency of the oscillator. In this way the oscillator 144 and driver 146 permit the tank circuit 150 to shift its frequency to remain at resonance despite a change in load. When the load on the secondary coil 52 decreases, the frequency of the oscillator 144 decreases in a manner essentially opposite that described above in connection with an increase in frequency. In summary, the decreased load results in decreased current in the tank circuit 150. This results, in turn, in a decrease in the voltage induced in the current transformer 232 and a decrease in the amplitude of the current feedback signal. The decreased current feedback signal has a decreased slope, and accordingly causes the operational amplifier 210 to complete the transition between saturation and cutoff later in time. The transistors 220 and 222 also transition later in time, thereby shifting the timing of the driver 146 and the timing of the switching circuit 148. The net effect of the shift in the timing of the switching circuit 148 is to shift, or "extend", the frequency and possibly vary the amplitude of the signal in the tank circuit 150. The extended signal is reflected into the current sensing circuit 218 where it is returned to the operational amplifier 210 to perpetuate the decrease in frequency of the oscillator 144. Optimal performance is achieved when the half-bridge switching circuit 148 alternates at the zero crossings of the current signal in the tank circuit 150. This provides optimal timing of the energy supplied by the switching circuit 148 to the tank circuit 150. In some applications, it may be necessary or desirable to shift the phase of the current feedback signal to provide the desired timing. For example, in some applications, the parasitic effect of the various circuit components may result in a shift in the phase of the current feedback signal. In such applications, the current sensing circuit can be provided with components, such as an RC circuit, to shift the signal back into alignment so that the switching circuit 148 alternates at the zero crossings. FIG. 17 illustrates a portion of an alternative current sensing circuit 218', which includes an RC circuit configured to shift the phase of the current feedback signal 120 degrees. In this embodiment, the current sensing circuit 218' is essentially identical to the current sensing circuit 218 of the above described embodiment, except that it includes two capacitors 800, 802 and two resistors 804, 806 that are connected along the leads extending back to the operation amplifier 210. FIG. 17 further illustrates that the secondary of the current transformer 232 can be connected to ground 182 to provide a zero reference, if desired. If the current transformer 232 is connected to ground 182, resistor 238 is eliminated.

Referring once again to FIG. 5, the output of the oscillator 144 is electrically connected with the driver 146. In the illustrated embodiment, the driver 146 is a multi-winding transformer that provides power to the half-bridge switching circuit 148. Transformer 246 is the preferred driver 146 in the illustrated embodiment because the phasing arrangement of the transformer 246 insures that the half-bridge switching circuit 148 will be alternately driven, which avoids cross conduction. A double arrangement of capacitors 248, 250 is electrically connected with the primary winding of transformer 246, thereby preventing DC current saturation in the transformer 246. Capacitor 246 is also connected with the ground connection 182 and capacitor 250 is also connected with the second DC power source 184.

The transformer 246 includes two secondary coils that are electrically connected to opposite legs of the half-bridge switching circuit 148 so that the half-bridge switching circuit 148 receives energy from transformer 246. The half-bridge switching circuit 148, which is also illustrated in FIG. 5, is electrically arranged as a MOSFET totem pole half-bridge switching circuit 252 that is driven by both secondary coils of transformer 246. The MOSFET totem pole half-bridge switching circuit 252 includes a first MOSFET transistor 254 and a second MOSFET transistor 256 that provide advantages over conventional bipolar transistor switching circuits. Energy is transferred from the driver 146 to the MOSFET transistors 254, 256 through a plurality of resistors 258, 260, 262, 264. The MOSFET transistors 254, 256 are designed to soft-switch at zero current and exhibit only conduction losses during operation. The output generated by MOSFET transistors 254, 256 is more in the form of a sine wave that has fewer harmonics than that generated by traditional bipolar transistors. Using MOSFET transistors 254, 256 also provides advantages by reducing radio frequency interference that is generated by the MOSFET transistors 254, 256 while switching during operation.

In the half-bridge switching circuit 148 depicted in FIG. 5, the first secondary coil of transformer 246 is connected with resistor 258 and resistor 260. The second secondary coil of transformer 246 is connected with resistor 262 and resistor 264. Resistor 260 is connected with the gate of MOSFET transistor 254 and resistor 264 is connected with the gate of MOSFET transistor 256. As illustrated, the first secondary coil of transformer 246 and resistor 258 are connected with the source of MOSFET transistor 254. The second secondary coil of transformer 246 and resistor 264 are connected with the gate of MOSFET transistor 256. The drain of MOSFET transistor 254 is connected with the second DC power source 184 and the source of MOSFET transistor 254 is connected with the drain of MOSFET transistor 256. The source of MOSFET transistor 256 and resistor 262 are connected with the ground connection 182.

A further benefit of the driver 146 is that multi-winding transformer 246 is a very convenient way to apply gate drive voltage to the MOSFET transistors 254, 256 that exceeds the second DC power source 184. The MOSFET transistors 254, 256 provide further advantages because they have diodes inherent in their design that protect the MOSFET totem pole half-bridge switching circuit 252 from load transients. In addition, over-voltages reflected from the series resonant tank circuit 150, by changes in load, are returned to supply rails by the inherent diodes within MOSFET transistors 254, 256.

Referring to FIG. 5, the output of the half-bridge switching circuit 148 is connected with the input of the series resonant tank circuit 150, which, in turn, inductively energizes the secondary coil 52 of the ultraviolet lamp assembly 14 (FIG. 4). As set forth above, in the illustrated embodiment of the invention, the current sensing circuit 218 of the oscillator 144 is connected with the output of the half-bridge switching circuit 148 and the input of the series resonant tank circuit 150 to provide current sense feedback to operational amplifier 210 of the oscillator 144 during operation. The primary coil of the transformer 232 is connected in series between the output of the half-bridge switching circuit 148 and the input of the series resonant tank circuit 150 as illustrated in FIG. 5.

Referring to FIG. 5, the series resonant tank circuit 150 comprises an inductive coupler 270, the parallel combination of a pair of tank capacitors 271, 272, a pair of diodes 274, 276 and a capacitor 278. The inductive coupler 270 is connected to the primary coil of transformer 232 and tank capacitors 271, 272. Tank capacitor 271 is also connected with the second DC power source 184 and tank capacitor 272 is also connected with the ground connection 182. In addition, tank capacitor 271 and the second DC power source 184 are connected with the anode of diode 274. The cathode of diode 274 and capacitor 278 are both connected with the second DC power source 184. Capacitor 278 is connected with the anode of diode 276 and the ground connection 182. Tank capacitor 272 is also connected the cathode of diode 276.

The series resonant tank circuit 150 sees all of the stray inductances of the component combination of the inductively coupled ballast circuit 103. This is relevant because the stray inductance, which is the combined inductance seen by the series resonant tank circuit 150, will limit the power transfer to the load (the ultraviolet light assembly 14) if its precludes the system from operating outside of resonance. The inductance of the secondary coil 52 and the resonant lamp circuit 152 are also reflected impedance values that help determine and limit the power that is delivered to the secondary coil 52 of the ultraviolet lamp assembly 14. In general, brute force oscillator/transformer combinations have power transfer limits because of stray and reflected inductance. In other words, the inductance of transformers and capacitors appears in series with the load thereby limiting power transfer capability.

In the illustrated embodiment, the frequency of operation for the series resonant tank circuit 150 is set near 100 KHz, which is determined by the inductance of the inductive coupler 270 and the parallel capacitance value of tank capacitors 271, 272, which are 0.1 uF capacitors in the illustrated embodiment. Tank capacitors 271, 272 must have low dissipation factors and be able to handle high levels of current, which is about 14 amps at start up. This resonant frequency may be adjusted up or down and has been selected only for convenient component selections. As noted above, the ballast circuit 103 seeks resonance through a feedback signal from the current sensing circuit 218. The current feedback signal is proportional to the current in the resonant tank circuit 150. The range of frequencies through which the ballast circuit 103 can search for resonance are readily varied by adjusting the values of the tank capacitors 271, 272. For example, by increasing the value of the tank capacitors 271, 272, the range can generally be decreased.

The inductive coupler 270 of the illustrated embodiment includes 10 turns of wire to generate the power required to inductively energize the secondary coil 52 in the ultraviolet lamp assembly 14. The inductive coupler 270 is preferably positioned in the outlet cup 36 (see FIG. 2A) of the water treatment system 10 and wire is wrapped around the outlet cup 36 in a diameter of about 3.5 inches. In the illustrated embodiment, litz wire is used for the inductive coupler 270 because litz wire is especially efficient in both performance and operating temperature, due to a skin effect caused by operating at 100 kHz. As set forth above, the inductive coupler 270 inductively energizes the secondary coil 52 of the ultraviolet lamp assembly unit 14 during operation.

Referring to FIG. 2A, the secondary coil 52 of the ultraviolet lamp assembly unit 14 is positioned in the outlet cup 36 and the inner sleeve shroud 26 when the water treatment system 10 is assembled. In the illustrated embodiment, the secondary coil 52 has 55 turns of small diameter wire that is wrapped around the secondary coil 52 in a diameter of about two inches. It is important to note that the coupling between the outlet cup 36 and the base subassembly 50, which houses the secondary coil 52, is designed to be very tolerant of gaps and misalignment. In fact, gaps are used to adjust the coupling coefficient, thereby adjusting the operating point of the ultraviolet lamp 60.

The permeance of the air gap between the inductive coupler 270 and the secondary coil 52 may be adjusted by changing the distance between the inductive coupler 270 and the secondary coil 52, as known in the art. As is apparent, the air gap within the air core transformer formed with the inductive coupler 270 and the secondary coil 52 may be selectively adjusted to limit power transfer from the inductive coupler 270 to the secondary coil 52. In addition, selective adjustment of the air gap may adjust the control response of the oscillator 144. Accordingly, selection of the permeance of the air gap balances overcurrent protection of the inductively coupled ballast circuit 103 with the bandwidth and responsiveness of the oscillator 144 when the secondary coil 52 is inductively energized.

As known in the art, inductive energization of the secondary coil 52 occurs when the inductive coupler 270 induces a magnetic flux in the air gap between the secondary coil 52 and the inductive coupler 270. In the illustrated embodiments, the magnetic flux is an alternating flux with a frequency that is preferably controlled by the oscillator 144 in an effort to maintain resonance.

During operation, the oscillator 144 may control the frequency at close to the resonant frequency of the series resonant tank circuit 150 and the ultraviolet lamp assembly unit 14. As previously discussed, the current sensing circuit 218 monitors the reflected impedance in the series resonance tank circuit 150 to allow the inductively coupled ballast circuit 103 to self-oscillate to a frequency which optimizes power transfer efficiency. If, for example, the impedance reflected by the ultraviolet light assembly 14 to the series resonant tank circuit 150 shifts slightly, the current sensing circuit 218 may adjust the frequency to correct for the shift in power transfer efficiency.

In the case where the impedance shifts significantly lower, such as, for example, when the ultraviolet lamp 60 fails in a shorted condition, the increase in current is limited by the air gap. As known in the art, the air gap functions to limit the amount of impedance that may be reflected. In addition, the impedance that is reflected may result in an impedance mismatch causing the reflection of power back to the series resonant tank circuit 150. As is readily apparent, the reflection of power to the series resonance tank circuit 150 may further limit power transfer to the secondary coil 52. Based on the combination of the air gap and the resonant frequency control, the inductively coupled ballast circuit 103 may be optimized for efficient operation while maintaining desirable levels of overcurrent protection.

The configuration of the air core transformer provides for simple and efficient replacement of the ultraviolet light assembly 14. In addition, the present invention provides further advantages by providing a coupling that does not require special contacts for the ultraviolet lamp assembly 14 because of the inductively coupled ballast circuit 103. Further, the configuration eliminates the need for conductors or other similar power transfer mechanism that may compromise waterproofing, corrode and/or otherwise malfunction.

As readily apparent to those skilled in the art, the inductively coupled ballast circuit 103 set forth above may be readily incorporated into other lighting systems or other systems requiring the transmission of electric power, and provides advantages over prior art ballast circuits because it drives lamps and other loads without requiring a physical connection and because it seeks resonance with the secondary. The inductively coupled ballast circuit 103 is also capable of instantaneously energizing several different styles of lamps, bulbs and other loads.

Referring once again to FIG. 5, the ballast feedback circuit 122 is electrically connected with the inductive coupler 270 of the series resonant tank circuit 150 and the control unit 102. The ballast feedback circuit 122 provides feedback to the control unit 102 while the inductively coupled ballast circuit 103 is driving the ultraviolet lamp 60. This allows the control unit 102 to monitor the energy being provided by the inductive coupler 270 to the secondary coil 52 of the ultraviolet lamp assembly 14. This provides the control unit 102 with the ability to determine if the ultraviolet lamp 60 is on or off and also, in other embodiments, the amount of current and voltage being applied to the ultraviolet lamp 60.

As depicted in FIG. 5, the ballast feedback circuit 122 includes an operational amplifier 280, a pair of resistors 282, 284, a pair of diodes 286, 288 and a capacitor 290. The signal from the series resonant tank circuit 150 is directed to the anode of diode 286. The cathode of diode 286 is connected with capacitor 290 and resistor 282. In addition, resistor 282 is connected with the anode of diode 288, resistor 284 and the positive input of operational amplifier 280. Resistor 284 is also connected with the positive input of operational amplifier 280 and the first DC power source 180. Capacitor 290 is also connected with the first DC power source 180, while the cathode of diode 288 is connected with the second DC power source 184. The negative input of operational amplifier 280 is connected directly with the output of operational amplifier 280. The output of operational amplifier 280 is connected with the control unit 102, thereby providing the feedback signal from operational amplifier 280 to the control unit 102.

Figure 6:
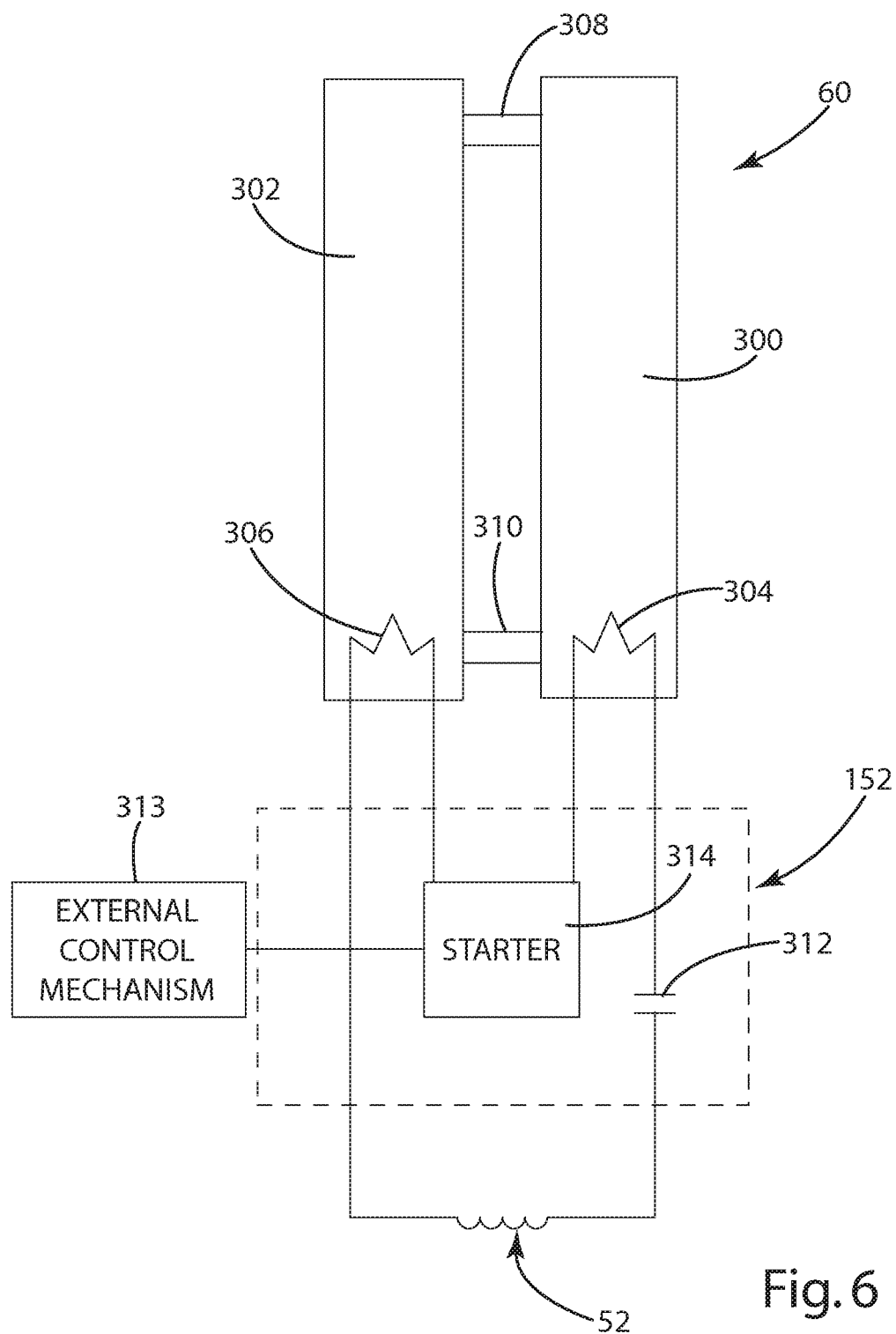
FIG. 6 depicts the secondary coil, the resonant lamp circuit and the ultraviolet lamp of the ultraviolet lamp assembly.

Referring to FIG. 6, the ultraviolet lamp assembly 14 of one embodiment includes the ultraviolet lamp 60, the resonant lamp circuit 152 and the secondary coil 52. The ultraviolet lamp 60 of the illustrated embodiment comprises a pair of bulbs 300, 302 and a pair of filaments 304, 306. The bulbs 300, 302 are held together with an upper connection bracket 308 and a lower connection bracket 310. The secondary coil 52 is connected with the resonant lamp circuit 152, which, in turn, is connected with the filaments 304, 306 of the ultraviolet lamp 60. The resonant lamp circuit 152 comprises a capacitor 312 that is electrically connected in series with the bulbs 300, 302 and a starter circuit 314 as illustrated.

Although an ultraviolet lamp assembly 14 is set forth in the illustrated embodiment of the present invention, as previously set forth, those skilled in the art would recognize that present invention is well-suited for use with other electromagnetic radiation emitting assemblies or light sources. For example, the ultraviolet lamp assembly 14 may use a pulsed white light lamp or a dielectric barrier discharge lamp to deactivate microorganisms in the flow of water. Those skilled in the art would recognize that the inductively coupled ballast circuit 103 may be used to drive not only various types of electromagnetic radiation emitting devices, but also other loads that might benefit from the wireless power supply or resonance-seeking characteristic of the present invention. As such, the present invention should not be limited to water treatment systems or lamps assemblies, but instead should be broadly interpreted to encompass a wide variety of power supply applications.

Figure 7:
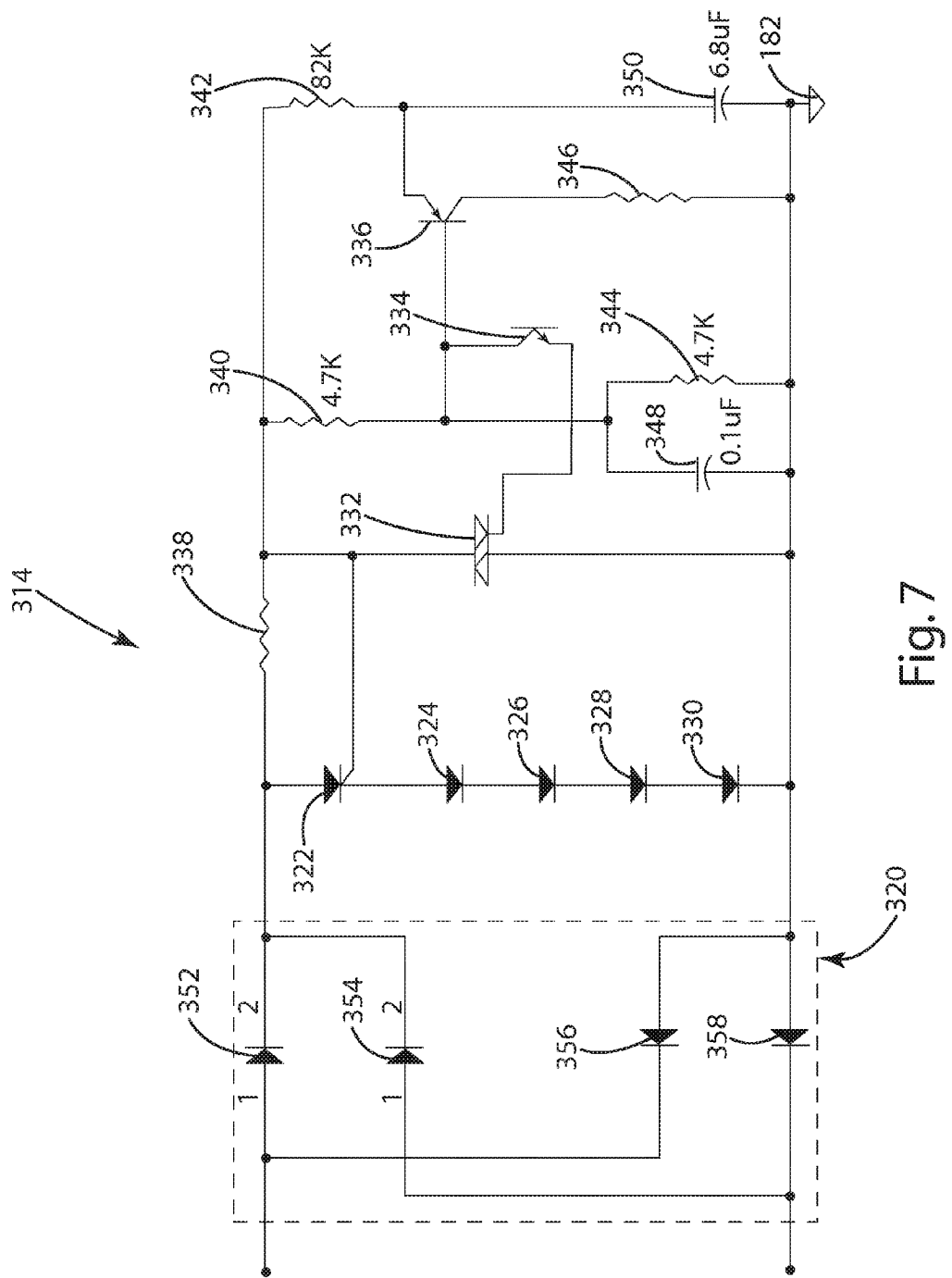
FIG. 7 is an electrical circuit schematic of the starter circuit.

As illustrated in FIG. 7, the starter circuit 314 comprises a bridge rectifier circuit 320, a silicon-controlled rectifier 322, a series arrangement of diodes 324, 326, 328, 330, a triac 332, a plurality of transistors 334, 336, a plurality of resistors 338, 340, 342, 344, 346 and a plurality of capacitors 348, 350. As those skilled in the art would recognize, the triac 332 may be any equivalent device, such as a FET transistor or a silicon controlled rectifier. In addition, those skilled in the art would recognize that the bridge rectifier circuit 320 comprises a plurality of diodes 352, 354, 356, 358 that are connected with the filaments 304, 306 of the ultraviolet lamp 60.

Referring to FIG. 7, the bridge rectifier circuit 320 is connected with silicon-controlled rectifier 322, resistor 338 and the ground connection 182. Silicon-controlled rectifier 322 is also connected with the series arrangement of diodes 324, 326, 328, 330 and the triac 332, which are both also connected with the ground connector 182. Resistor 338 is connected with triac 332, resistor 340 and resistor 342. Resistor 340 is connected with the collector of transistor 334, the base of transistor 336, capacitor 348 and resistor 344. Capacitor 348 and resistor 344 are further connected with the ground connection 182. Resistor 342 is connected with the emitter of transistor 336 and capacitor 350, which is also connected with the ground connection 182. The gate of triac 332 is connected with the emitter of transistor 334. The collector of transistor 336 is connected with the base of transistor 334 and resistor 346. Resistor 346 is connected with the ground connection 182 to complete the starter circuit 314.

Referring back to FIG. 6, during operation, capacitor 312 limits the current supplied to the ultraviolet lamp 60 from the secondary coil 52 by changing the reflected impedance of the ultraviolet lamp 60 through the inductive coupler 270 (see FIG. 5) of the series resonant tank circuit 150. As is apparent, by selecting the value of capacitor 312 in view of the impedance of the ultraviolet lamp 60 and the secondary coil 52, the ultraviolet lamp assembly 14 may be impedance matched with the power source (the series tank circuit 150). In addition, the ultraviolet lamp assembly 14 may be tuned to resonate at a frequency similar to the resonant frequency of the series resonant tank circuit 150, thereby optimizing coupling and minimizing reflected power.

The starter circuit 314 is designed to short filaments 304, 306 during start-up, thereby causing maximum preheat of the bulbs 300, 302. This allows the ultraviolet lamp 60 to strike maximum dispersion of the mercury in bulbs 300, 302, thereby causing maximum intensity and delivering the highest dose of ultraviolet light to the water as it passes through the ultraviolet lamp assembly 14. In other words, the starter circuit 314 is designed so that the ultraviolet lamp 60 instantly turns on at maximum intensity. The placement of mercury in bulbs 300, 302 is important for maximum output. When the mercury condenses within the plasma path, the mercury is dispensed more evenly throughout bulbs 300, 302. The faster dispersion also allows quicker peak intensity, thereby providing the ability to give the flow of water a faster, more intense dose of ultraviolet light at start-up. As is apparent, the shorting of the starter circuit 314 allows maximum power transfer while maintaining optimum power transfer efficiency since impedance matching remains in place. It is further apparent from the foregoing discussion that the air gap functions to provide current limiting during startup while still providing sufficient power transfer to the secondary coil to almost instantly start the ultraviolet light 60 at maximum intensity.

Referring to FIG. 2B, the O-ring 62 acts as a heat sink and is purposefully placed between the path of water, which flows through the pair of quartz tubes 58, and the ultraviolet lamp 60 plasma path to allow the mercury to condense within the plasma path for improved instant ultraviolet light output. Referring again to FIG. 6, as the ultraviolet lamp 60 is energized, the full-circuit voltage potential is applied across capacitor 312, filaments 304, 306 and the starter circuit 314. Because of the low impedance value of the filaments 304, 306 and the starter circuit 314, which acts as a short at start-up, the current is high for maximum preheat of the ultraviolet lamp 60. This causes the preheat of the ultraviolet lamp 60 to disperse some initial mercury at start-up. When the starter circuit 314 heats up, the starter circuit 314 RC time constant releases the shorting device, which is the triac 332 (FIG. 7) in one embodiment, thereby providing full voltage across the filaments 304, 306. In other embodiments, the shorting device may be other mechanisms such as, for example, electromagnetically controlled reed switches, an optically controlled triac and/or any other device capable of moving between a contacting and non-contacting state. In addition, the shorting device may be controlled by an external control mechanism such as, for example, electromagnet control signals, radio frequency control signals, optical control signals or any other mechanism capable of communicating some form of signal to the shorting device absent conductors therebetween. The starter circuit 314 allows a better start than a thermister because thermisters consume more energy after opening and do not open as quickly. In addition, as is apparent, operation of the starter circuit 314 occurs in a stand-alone fashion without external control wires or other features that may compromise water tightness and/or replacement ability of the ultraviolet light assembly 14.

Figure 8:
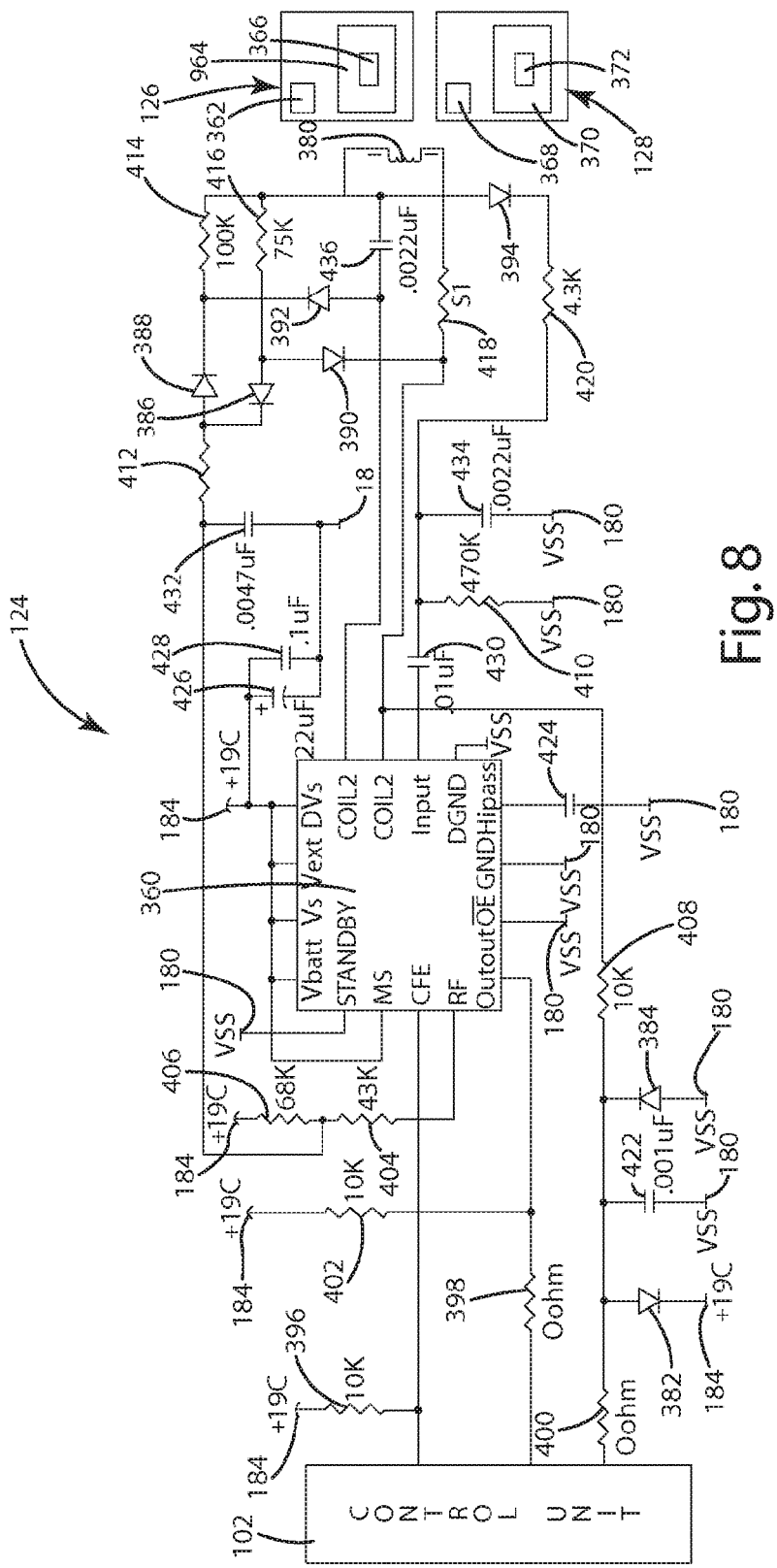
FIG. 8 illustrates an electrical circuit schematic of the radio frequency identification system used in the water treatment system

Referring to FIG. 8, one radio frequency identification system 124 is illustrated electrically connected with the control unit 102. The radio frequency identification system 124 uses a base station to communicate with the ultraviolet light radio frequency identification transponder 126 and the filter radio frequency identification transponder 128. The radio frequency identification system 124 allows contactless reading and writing of data, which is transmitted bidirectionally between the base station 360 and the transponders 126, 128. In one embodiment, the radio frequency identification system 124 is manufactured by TEMIC Semiconductors under model number TR5551A-PP.

The radio identification system 124 is used by the control unit 102 to keep track of information specific to each ultraviolet lamp assembly 14 and filter assembly 16. As previously set forth, the ultraviolet lamp assembly 14 and the filter assembly 16 are both designed to be readily replaceable. Since the ultraviolet light radio frequency identification transponder 126 and the filter radio frequency transponder 128 are located in the ultraviolet lamp assembly 14 or the filter assembly 16, these devices are never separated, which allows the control unit 102 to read and write information to and from the transponders 126, 128 through the base station 360.

Referring once again to FIG. 8, the ultraviolet light radio frequency identification transponder 126 includes a transponder antenna 362 and a read/write IDIC® (e5551) chip 364. The read/write IDIC® (e5551) chip further includes an EEPROM device 366 that physically stores the relevant information for each respective ultraviolet lamp assembly 14 in memory locations. In the illustrated embodiment, the information consists of an ultraviolet lamp serial number, ultraviolet lamp start limit, ultraviolet lamp on-time limit, ultraviolet lamp install time limit, ultraviolet lamp cycle on-time, cycle mode low temperature, minimum ultraviolet lamp on-time, ultraviolet lamp high-mode time and ultraviolet lamp preheat time. In addition, the EEPROM device 366 in the ultraviolet light radio frequency identification transponder 126 allows the control unit 102 to keep track of ultraviolet lamp install time, ultraviolet lamp powered time, ultraviolet lamp starts and total ultraviolet lamp cold starts.

The ultraviolet lamp serial number is unique to each ultraviolet lamp assembly 14 and allows the control unit 102 of the water treatment system 10 to keep track of which ultraviolet lamp assemblies 14 have been installed in the water treatment system 10. The ultraviolet lamp start limit relates to the maximum allowed number of ultraviolet lamp starts and the ultraviolet lamp on-time limit relates to the maximum allowed installation time for the ultraviolet lamp 60. The ultraviolet lamp install time limit relates to the maximum allowable installation time for the ultraviolet lamp assembly 14 and the ultraviolet lamp cycle on-time relates to the minimum amount of time the ultraviolet lamp 60 needs to be energized in low-temperature mode. The cycle mode low-temperature information relates to the temperature value to which the water treatment system 10 switches to low-temperature mode and the minimum ultraviolet lamp on-time relates to the minimum amount of time the ultraviolet lamp 60 must remain energized. The ultraviolet lamp high-mode time information relates to the amount of time the ultraviolet lamp 60 operates in high mode and the ultraviolet lamp preheat time relates to the amount of time the ultraviolet lamp 60 needs to be preheated.

As previously set forth, the EEPROM device 366 in the ultraviolet light radio frequency identification transponder 126 is also capable of keeping track of the ultraviolet lamp install time. This information tracks the number of hours that the current ultraviolet lamp 60 has been plugged into the water treatment system 10. In one embodiment, for every minute the ultraviolet lamp 60 is plugged into the water treatment system 10, one minute is added to the total. The EEPROM device 366 also keeps track of the ultraviolet lamp powered time and the total ultraviolet lamp powered time. The ultraviolet lamp powered time and the total ultraviolet lamp powered time keeps track of the amount of time the ultraviolet lamp 60 has been on so that the control unit 102 can determine if a new ultraviolet lamp assembly 14 needs installed. The ultraviolet lamp starts memory location stores the number of times the ultraviolet lamp 60 has been started, so that the control unit 102 can use this information to determine the end of life of the ultraviolet lamp 60. The total ultraviolet lamp cold-starts memory location tracks the number of times the ultraviolet lamp 60 has been started when the ambient temperature sensor 114 indicates that the temperature is below a predetermined threshold value.

Referring once again to FIG. 8, the filter radio frequency identification transponder 128 includes a transponder antenna 368 and a read/write IDIC® (e5551) chip 370. The read/write IDIC® (e5551) chip 370 further includes an EEPROM device 372 that physically stores the relevant information for each respective filter assembly 16 in memory locations. In the described embodiment, the relevant information consists of a filter assembly serial number, a filter assembly volume limit, a filter assembly install time limit, and a plugged filter assembly threshold percent.

The filter assembly serial number is used for unique identification of different filter assemblies 16 so that the control unit 102 can monitor which filter assemblies 16 have been installed in the water treatment system 10. The filter assembly volume limit is associated with the volume of water the filter assembly is designed to filter before reaching the end of its useful life. The filter assembly install time limit is used by the control unit 102 to compute the remaining life of the filter assembly 16 based on a predetermined allowable wet time. The plugged filter assembly threshold percent contains the maximum allowable percentage of flow reduction for the filter assembly 16 before it needs replaced. This maintains the percent of degradation of the filter assembly 16 before a plugged filter assembly 16 error is initiated by the control unit 102.

The radio frequency identification system 124 includes the base station 360, a coil 380, a plurality of diodes 382, 384, 386, 388, 390, 392, 394, a plurality of resistors 396, 398, 400, 402, 404, 406, 408, 410, 412, 414, 416, 418, 420 and a plurality of capacitors 422, 424, 426, 428, 430, 432, 434, 436 that are electrically connected as illustrated in FIG. 8. Those skilled in the art would recognize that the connection of the aforementioned components is well known to those skilled in the art. The radio frequency identification system 124 has been installed in the water treatment system 10 using specifications set forth for the TK5551A-PP, which, as previously set forth, is manufactured by TEMIC Semiconductors. For the purpose of the present invention, it is important to note that the base station 360 uses the coil 380 for bidirectional communication with the ultraviolet light radio frequency identification transponder 126 and the filter radio frequency identification transponder 128.

The control unit 102 is electrically connected with the base station 360 so that the control unit 102 can communicate with the base station 360. As such, the control unit 102 is capable of reading and writing information to and from the ultraviolet light radio frequency identification transponder 126 and the filter radio frequency identification transponder 128 through the base station 360 by using the coil 380. The radio frequency identification system 124 is connected with the first DC power source 180 and the second DC power source 184 as illustrated in FIG. 8, which provides the radio frequency identification system 124 with energy to function during operation.

Those skilled in the art would recognize that other identification systems could be used with the present invention, such as contact-type identification systems. However, the illustrated embodiment of the invention uses a radio frequency identification system 124 because of the inherent benefits such a system provides.

Figure 9:
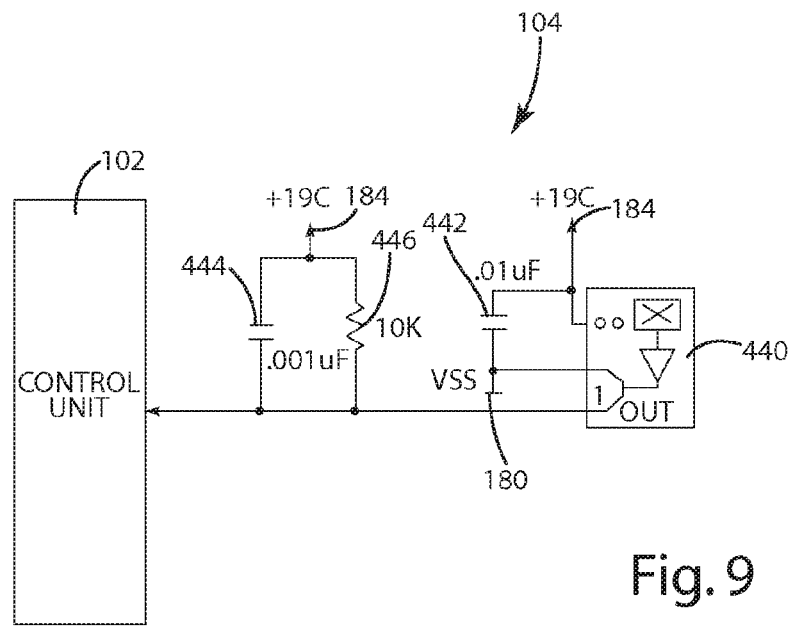
FIG. 9 is an electrical circuit schematic of the flow sensor circuit.

Referring to FIG. 9, the flow sensor circuit 104 is connected with the control unit 102 to provide electrical signals to the control unit 102 indicating that water is flowing through the water treatment system 10. The flow sensor circuit 104 includes a flow sensor 440, a plurality of capacitors 442, 444 and a resistor 446. The flow sensor is manufactured by Allegro under model number 3134. Capacitor 442 is connected with the flow sensor 440, the first DC power source 180 and the second DC power source 184. The output of the flow sensor 440 is connected with the parallel combination of resistor 446 and capacitor 444, before being connected with the control unit 102. Resistor 446 and capacitor 444 are also connected with the second DC power source 184. During operation, the flow sensor 440 delivers electrical signals to the control unit 102, which indicates that water is flowing in the water treatment system 10, thereby causing the control unit 102 to instantaneously energize the ultraviolet lamp 60. Those skilled in the art would recognize that several variations exist on the disclosed flow sensor circuit 104 and that the disclosed flow sensor circuit 104 is provided by way of example only and should be not construed as a limitation of the present invention.

Figure 10:
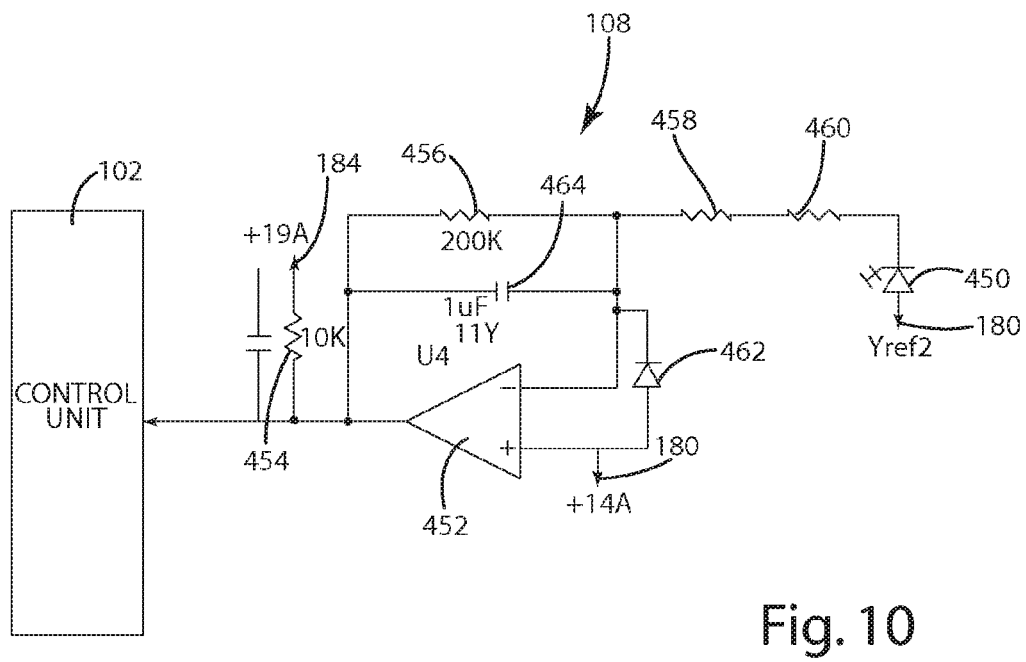
FIG. 10 is an electrical circuit schematic of the ambient light sensor circuit.

Referring to FIG. 10, the ambient light sensor circuit 108 comprises a photosensitive diode 450, an operational amplifier 452, a plurality of resistors 454, 456, 458, 460, a diode 462 and a capacitor 464 electrically connected as illustrated. For purposes of the present invention, it is sufficient to note that the photosensitive diode 450 provides electrical signals to the negative input of the operational amplifier 452, which, in turn, conditions the signal for the control unit 102. The ambient light sensor circuit 108 is powered by the first DC power source 180 and the second DC power source 184. 10. Those skilled in the art would recognize that several variations exist on the design of ambient light sensor circuits 108 and that the illustrated embodiment should not be construed as a limitation on the present invention.

Figure 11:
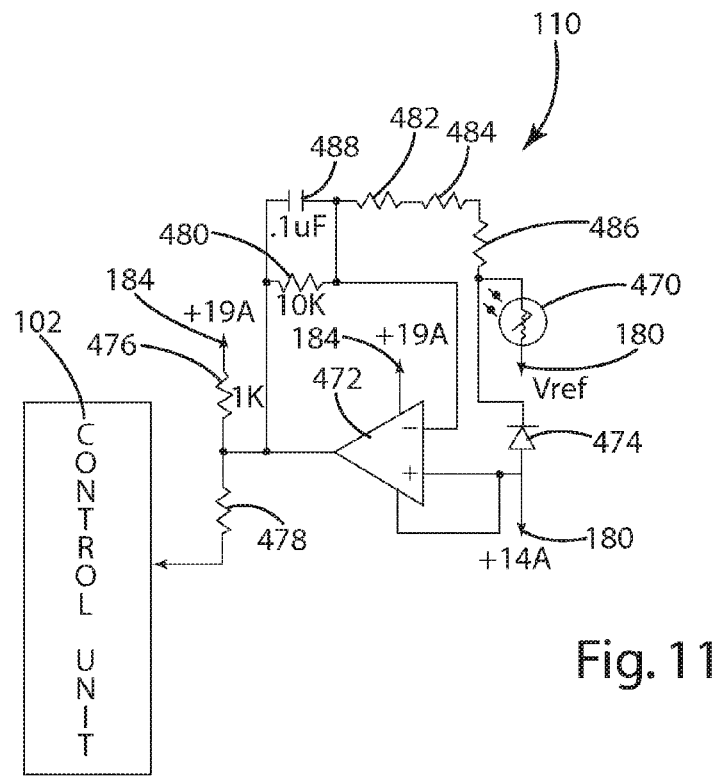
FIG. 11 is an electrical circuit schematic of the ultraviolet light sensor circuit.

Referring to FIG. 11, as previously set forth, the visible light sensor circuit 110 is connected with the control unit 102 to provide electrical signals to the control unit 102 corresponding to the intensity of the ultraviolet lamp 60 during operation. In one embodiment, the visible light sensor circuit 110 comprises a photosensitive resistor 470, an operational amplifier 472, a diode 474, a plurality of resistors 476, 478, 480, 482, 484, 486 and a capacitor 488 electrically connected as depicted in FIG. 11. In addition, the visible light sensor circuit 110 is powered by the first DC power source 180 and the second DC power source 184. Those skilled in the art would recognize that the visible light sensor circuit 110 takes the electrical signal generated by the photosensitive resistor 470 and amplifies it with the operational amplifier 472, before being directed to the control unit 102. Further, those skilled in the art would recognize that the design of visible light sensor circuits 110 can vary and that the disclosed ultraviolet light sensor circuit 110 is by way of example only and should not be construed as a limitation of the present invention.

Figure 12:
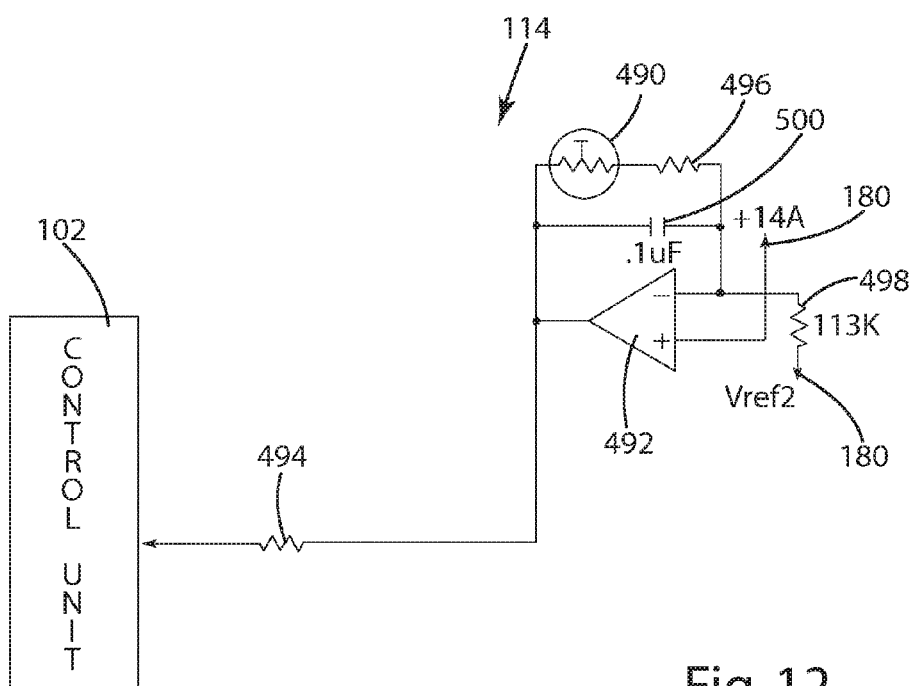
FIG. 12 is an electrical circuit schematic of the ambient temperature sensor circuit.

Referring to FIG. 12, as previously set forth, one ambient temperature sensor circuit 114 is connected with the control unit 102 to provide the control unit 102 with electrical signals that change with corresponding changes in the ambient temperature. The ambient temperature sensor circuit 114 comprises a thermistor 490, an operational amplifier 492, a plurality of resistors 494, 496, 498 and a capacitor 500 that are electrically connected as illustrated in FIG. 12. During operation, the voltage drop across thermistor 490 changes as the ambient temperature changes, thereby causing the electrical signal that is sent from the output of the operational amplifier 492 to the control unit 102 to either increase or decrease. Those skilled in the art would recognize that the design of ambient temperature sensor circuits 114 can vary. One ambient temperature sensor circuit 114 illustrated in FIG. 12 is by way of example only and should not be construed as a limitation of the present invention.

Figure 13:
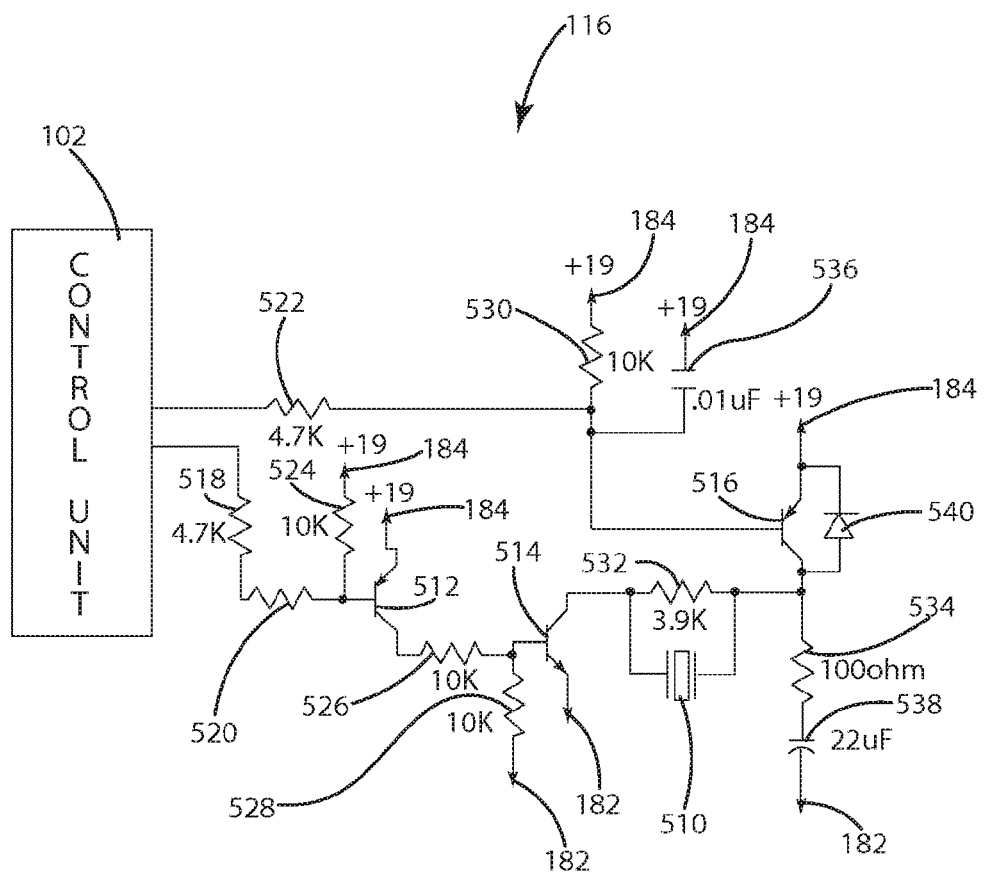
FIG. 13 is an electrical circuit schematic of the audible generation circuit.

Referring to FIG. 13, as previously set forth, one audio generation circuit 116 is connected with the control unit 102 for generating audible enunciations in response to predetermined system states. One audio generation circuit 116 comprises a piezoelectric element 510, a plurality of transistors 512, 514, 516, a plurality of resistors 518, 520, 522, 524, 526, 528, 530, 532, 534, a plurality of capacitors 536, 538 and a diode 540, which are electrically connected as depicted in FIG. 13. As readily apparent to those skilled in the art, the control unit 102 is capable of energizing the piezoelectric element 510, thereby causing the piezoelectric element 510 to generate audible tones through vibrations. Those skilled in the art would recognize that several devices and circuits exist that are capable of generating audible tones. The presently disclosed audio generation circuit 116 is by way of example only and likewise should not be construed as a limitation of the present invention.

Figure 14:
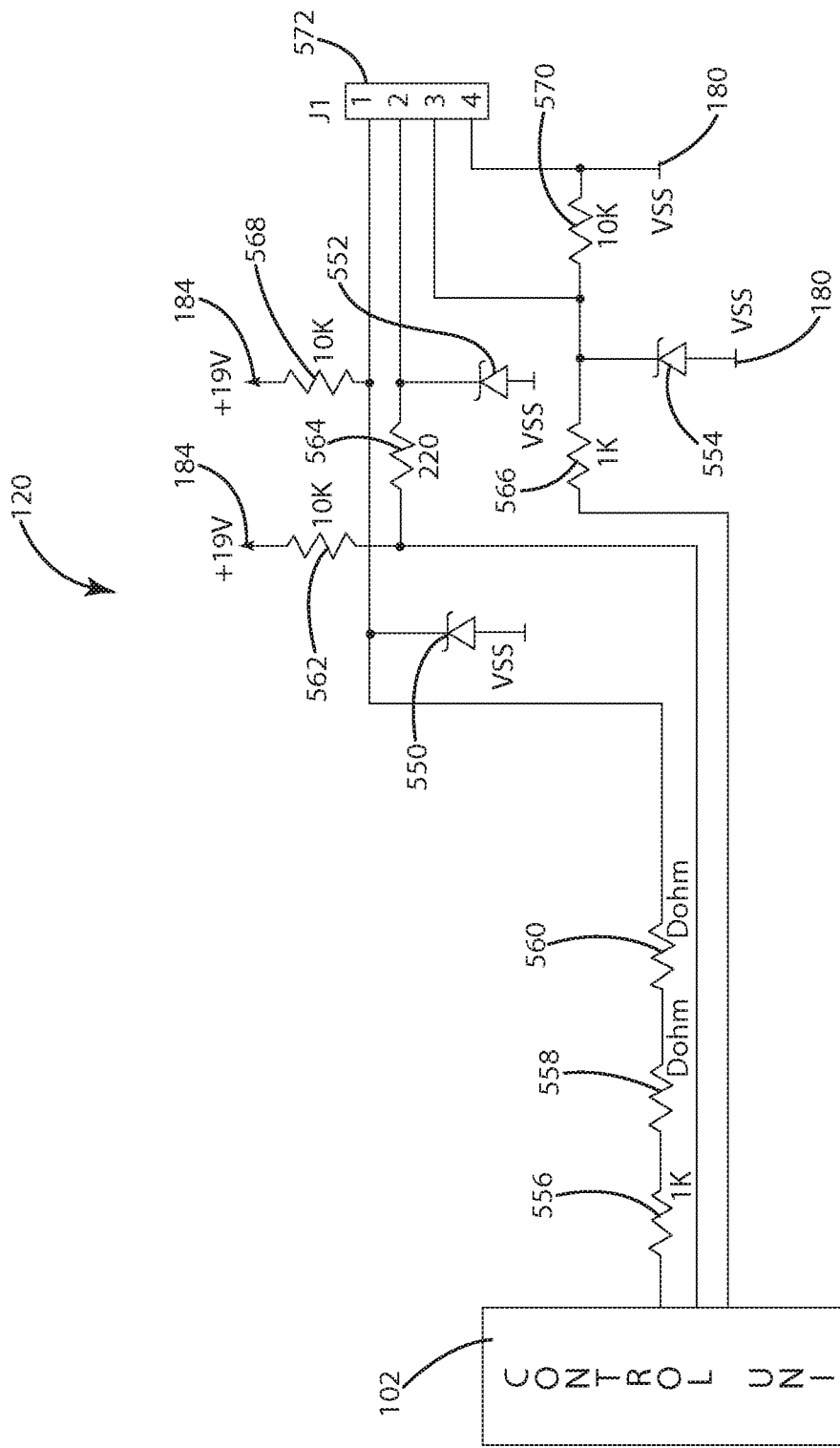
FIG. 14 is an electrical circuit schematic of the communication port.

Referring to FIG. 14, as previously set forth, the communications port 120 is connected with the control unit 102. The communications port 120 is used by the control unit 102 to communicate bidirectionally with a peripheral device (not shown), such as a personal computer or a hand-held device. In one embodiment, the communications port 120 comprises a plurality of zenar diodes 550, 552, 554 and a plurality of resistors 556, 558, 560, 562, 562, 566, 568, 570, which are electrically connected as illustrated in FIG. 14. The first DC power source 180 and the second DC power source 184 provide power to the communications port 120. The communications port 120 is designed to use the RS-232 communications standard, as well known in the art. A port connector 572 is provided so that the peripheral device can be connected with the communications port 120. Those skilled in the art would recognize that different types of communication ports may be used and are beyond the scope of the present invention. To that end, one communications port 120 disclosed herein is by way of example only and should not be construed as a limitation of the present invention.

In one embodiment, the ballast circuit 103 also includes a current limit circuit 700 designed to monitor the current produce by the circuit, and shut the circuit down when it falls outside of desired parameters. The current limit circuit 700 can be configured to disable the ballast circuit 103 when a current threshold is exceeded (i.e. an upper limit) or when the current falls outside of a range (i.e. both upper and lower limits). Upper and lower limits are particularly useful in applications where low current and unstable operation can damage the load, for example, in lighting applications where a dimming function is achieved by increasing the air gap between the primary coil and the secondary coil.

Figure 16:
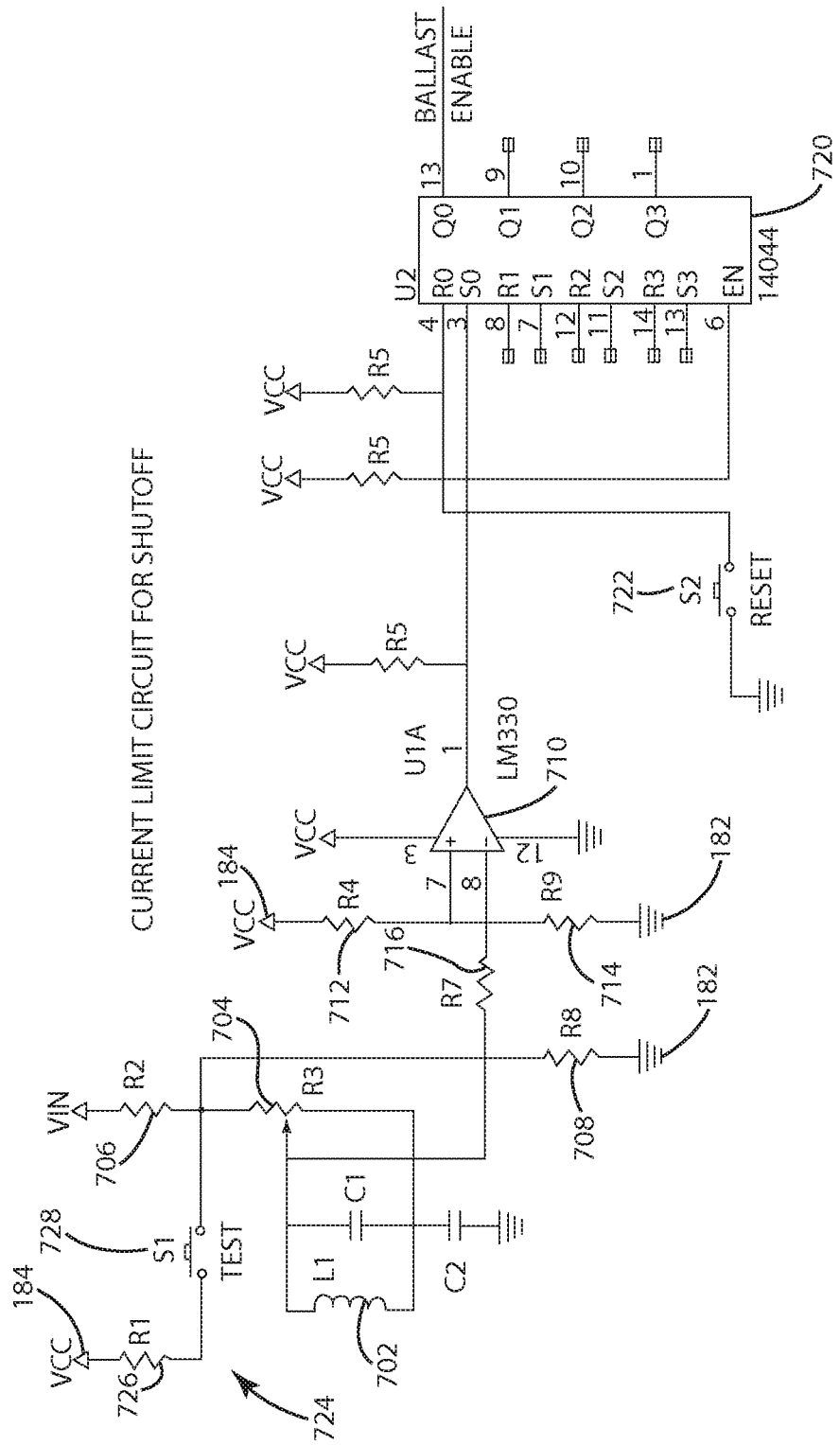
FIG. 16 is an electrical circuit schematic of the current limit circuit.

One embodiment of the current limit circuit 700 is shown in FIG. 16. The current limit circuit 700 includes a current sensing transformer 702 that produces current proportional to the flow of current to the primary coil 270. The current transformer 702 is preferably created by forming a coil of wire around the core of the current sensing transformer 232 of the current sensing circuit 218. The current from the current transformer 702 develops a voltage across resistor 704. Another resistor 706 is tied to the input voltage of ballast circuit. The relationship to the input voltage causes the level to shift as the input voltage shifts. This permits the current transformer 702 to track the real performance even as input voltage shifts. Resistor 708 allows a voltage bias from ground that helps to raise the variable current transformer voltage to a level detectable by the operational amplifier 710. Resistors 712 is connected between voltage source 184 and the positive input of operational amplifier 710. Resistor 714 is connected between ground connection 182 and the positive input of operational amplifier 710. Resistors 712 and 714 establish a limit or threshold to set the operating and non-operating modes. Resistor 716 is connected between the current transformer 70 and the negative input lead of operational amplifier 710 to prevent the operational amplifier 710 from drawing too much current from the current transformer 102. The output of the operational amplifier 702 is connected to integrated circuit 720, which is preferably a conventional latch or flip-flop, such as IC 14044. When the output from the operational amplifier 702 is driven high, the latch is triggered, thereby latching the disable signal. The integrated circuit 720 preferably maintains the ballast circuit 103 in the disabled condition until the manual reset switch 722 is pressed or otherwise actuated. Alternatively, the reset switch 722 can be replaced by a timer circuit (not shown) that resets the current limit circuit 700 after a defined period of time. The current limit circuit 700 may also include a test circuit 724 that permits testing of the operation of the current limit circuit 700. The test circuit 724 is connected to power source 184 and includes resistor 726 and switch 728. When switch 728 is depressed or otherwise actuated, current in excess of the threshold is applied to the operational amplifier 710. If operating properly, this current will cause the current limit circuit 700 to disable the ballast circuit 103.

As an alternative, the current from the current transformer 702 can be monitored by a microprocessor that is programmed to disable the ballast circuit when the current exceeds the desired threshold or falls outside of the desired range. In some applications, however, the microprocessor may not provide sufficient speed to provide acceptable response times. Accordingly, the hardware embodiment described may be preferable in some application.

While the invention has been described in its currently best known modes of operation and embodiments, other modes and embodiments of the invention will be apparent to those skilled in the art and are contemplated. In addition, although one embodiment of the present invention is directed to a water treatment system 10, those skilled in the art would recognize that the present invention may be readily incorporated in several different types of fluid treatment systems.

The invention claimed is:

1. A non-contact power transfer system comprising:
   a non-contact power supply including:
      a primary subcircuit having a primary;
      a sensor configured to sense a characteristic of power that changes over time, said sensor configured to provide a first sensor output indicative of said characteristic of power at a first time, said sensor configured to provide a second sensor output indicative of said characteristic of power at a second time different from said first time;
      a control circuit supplying power to said primary, said control circuit making an adjustment of an operational characteristic of said non-contact power supply based on both said first sensor output and said second sensor output;
   an electronic device separable from said non-contact power supply, said electronic device being absent from physical interconnection with said non-contact power supply and absent from electrical connection with said non-contact power supply, said electronic device and said non-contact power supply capable of inductively coupling when in sufficient proximity to each other said electronic device includes:
      a secondary for inductively coupling with said primary, said secondary being absent from physical interconnection with said primary, said secondary being absent from electrical connection with said primary, wherein said primary is capable of inductively energizing said secondary; and
      a load electrically connected to said secondary, whereby power is provided to said load by said secondary;
   whereby said electronic device is readily placeable in sufficient proximity to said non-contact power supply to inductively receive power without the need to make electrical connection with said non-contact power supply and without the need to make physical interconnection with said non-contact power supply; and
   whereby said electronic device is readily removable from the sufficient proximity of said non-contact power supply without the need to disconnect electrical connection with said non-contact power supply and without the need to disconnect physical interconnection with said non-contact power supply.

2. The non-contact power transfer system of claim 1 wherein said sensor senses said characteristic of power in said primary subcircuit.

3. The non-contact power transfer system of claim 1 wherein said operational characteristic is an operating frequency of said primary subcircuit.

4. The non-contact power transfer system of claim 1 wherein said sensor is a current sensor, and wherein said characteristic of power sensed by said sensor is a current of power in said primary subcircuit.

5. The non-contact power transfer system of claim 4 wherein said first sensor output is indicative of said current of power at said first time, wherein said second sensor output is indicative of said current of said power at said second time, and wherein said adjustment is proportional to a change in current over time from said first sensor output to said second sensor output.

6. The non-contact power transfer system of claim 4 wherein said control circuit includes an operational amplifier operably coupled to said current sensor and a buffer circuit, wherein an output of said operational amplifier is electrically coupled to a driver circuit through said buffer circuit, and wherein said driver circuit is configured to control supply of power to the primary subcircuit based on said output of said operational amplifier.

7. The non-contact power transfer system of claim 6 wherein said output of said operational amplifier at said first time is based on said first sensor output, wherein said output of said operational amplifier is operably coupled to a negative lead of said operational amplifier.

8. The non-contact power transfer system of claim 7 wherein, at said second time, said second sensor output is operably coupled to a positive lead of said operational amplifier, wherein said operational amplifier makes an adjustment to said output based on a difference between a signal on said positive lead and a signal on said negative lead.

9. The non-contact power transfer system of claim 1 wherein said control circuit is configured to make a plurality of adjustments of said operational characteristic over time, wherein each of said plurality of adjustments is based on at least two sensor outputs obtained from said sensor at different points in time.

10. The non-contact power transfer system of claim 1 wherein said load is further defined as a resonant lamp circuit.

11. The non-contact power transfer system of claim 1 wherein said primary is disposed in a series resonant tank circuit.

12. The non-contact power transfer system of claim 1 wherein said load includes an electromagnetic radiation emitting device.

13. The non-contact power transfer system of claim 1 wherein said load is one of an ultraviolet lamp, an incandescent lamp, a light emitting diode lamp, a pulsed white light lamp and a dielectric barrier discharge lamp.

14. The non-contact power transfer system of claim 1 wherein an amplitude of said characteristic of power varies as a function of changes in said load.

15. The non-contact power transfer system of claim 14 wherein changes in said load include at least one of installation of said load, removal of said load, positional changes of said load with respect to said non-contact power supply, changes in impedance of said load, changes in temperature of said load, and changes in impedance over the life of said load.

16. The non-contact power transfer system of claim 1 wherein said control circuit is configured to make said adjustment based on a single type of sensor output.

17. The non-contact power transfer system of claim 16 wherein said single type of sensor output is a current in said primary.

18. A method for supplying power from a wireless power supply to an electronic device through an inductive coupling, comprising the steps of:
- removably placing at least one of a secondary of the electronic device and a primary of the wireless power supply into sufficient proximity of the other absent of physical interconnection between the electronic device and the wireless power supply and absent of electrical connection between the electronic device and the wireless power supply;
- supplying a power at a frequency to the primary to transfer power across an inductive coupling between the primary and the secondary absent of physical interconnection between the primary and the secondary, and absent of electrical connection between the primary and the secondary;
- generating power within the secondary across the inductive coupling, the generated power being applied to the load of the electronic device;
- sensing a characteristic of power in the wireless power supply at a first time to generate a first sensor output, the sensed characteristic of power being affected by a characteristic of the load reflected through the inductive coupling;
- sensing the characteristic of power in the wireless power supply at a second time different from the first time to generate a second sensor output;
- making an adjustment to an operational characteristic of the power supplied to the primary based on both the first sensor output and the second sensor output;
- whereby the electronic device is readily placeable in sufficient proximity to the non-contact power supply to inductively receive power without the need to make electrical connection with the non-contact power supply and without the need to make physical interconnection with the non-contact power supply; and
- whereby the electronic device is readily removable from the sufficient proximity of the non-contact power supply without the need to disconnect electrical connection with the non-contact power supply and without the need to disconnect physical interconnection with the non-contact power supply.

19. The method of claim 18 wherein the characteristic of the power includes current in the primary.

20. The method of claim 18 wherein the operational characteristic of power includes said frequency of said power supplied to said primary.

21. An inductive power supply for supplying power inductively to an electronic device separable from the inductive power supply, the inductive power supply comprising:
- a primary circuit including a primary configured to inductively couple with a secondary of the electronic device to transfer power to the electronic device without a physical connection with electronic device and without an electrical connection with the electronic device, wherein said primary is capable of inductively coupling with the electronic device when in sufficient proximity to the electronic device;
- a sensor configured to sense a characteristic of power in the inductive power supply that changes over time, said sensor configured to provide a first sensor output indicative of said characteristic of power at a first time, said sensor configured to provide a second sensor output indicative of said characteristic of power at a second time different from said first time;
- a control circuit for supplying power to said primary, said control circuit configured to make an adjustment of an operational characteristic of the inductive power supply based on both said first sensor output and said second sensor output;
- whereby the electronic device is readily placeable in sufficient proximity to said primary circuit to inductively receive power without the need to make electrical connection with said primary circuit and without the need to make physical interconnection with said primary circuit; and
- whereby the electronic is readily removable from the sufficient proximity of said primary circuit without the need to disconnect electrical connection with said primary circuit and without the need to disconnect physical interconnection with said primary circuit.

22. The inductive power supply of claim 21 wherein said sensor senses said characteristic of power in said primary circuit.

23. The inductive power supply of claim 22 wherein said sensor is a current sensor, and wherein said characteristic of power sensed by said sensor is a current of power in said primary subcircuit.

24. The inductive power supply of claim 23 wherein said first sensor output is indicative of said current of power at said first time, and wherein said second sensor output is indicative of said current of said power at said second time, and wherein said adjustment is proportional to a change in current over time from said first sensor output to said second sensor output.

25. The non-contact power transfer system of claim 23 wherein said control circuit is configured to make said adjustment based on a single type of sensor output, wherein both said first sensor output and said second sensor output are said single type of sensor output.

26. The non-contact power transfer system of claim 25 wherein said single type of sensor output is a current in said primary.

27. The inductive power supply of claim 21 wherein said control circuit is configured to make a plurality of adjustments of said operational characteristic over time, wherein each of said plurality of adjustments is based on at least two sensor outputs obtained from said sensor at different points in time.

28. The inductive power supply of claim 21 wherein said operational characteristic is an operating frequency of said primary circuit.

29. The inductive power supply of claim 21 wherein said first and second sensor outputs are indicative of an amplitude of said characteristic of power.

* * * * *